United States Patent
Wang et al.

(10) Patent No.: US 11,468,570 B2
(45) Date of Patent: *Oct. 11, 2022

(54) METHOD AND SYSTEM FOR ACQUIRING STATUS OF STRAIN AND STRESS OF A VESSEL WALL

(71) Applicant: SHANGHAI UNITED IMAGING HEALTHCARE CO., LTD., Shanghai (CN)

(72) Inventors: Hongjian Wang, Shanghai (CN); Jieyan Ma, Shanghai (CN); Yuan Ren, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 99 days.

This patent is subject to a terminal disclaimer.

(21) Appl. No.: 17/017,648

(22) Filed: Sep. 10, 2020

(65) Prior Publication Data

US 2020/0410685 A1 Dec. 31, 2020

Related U.S. Application Data

(63) Continuation of application No. 15/638,626, filed on Jun. 30, 2017, now Pat. No. 10,861,158, which is a
(Continued)

(51) Int. Cl.
*G06T 7/00* (2017.01)
*G06T 17/00* (2006.01)
(Continued)

(52) U.S. Cl.
CPC ........ *G06T 7/0016* (2013.01); *A61B 5/02007* (2013.01); *A61B 5/7278* (2013.01);
(Continued)

(58) Field of Classification Search
None
See application file for complete search history.

(56) References Cited

U.S. PATENT DOCUMENTS

| 6,236,738 B1 | 5/2001 | Zhu et al. |
| 6,385,332 B1* | 5/2002 | Zahalka .................... G06T 7/12 |
| | | 382/128 |

(Continued)

FOREIGN PATENT DOCUMENTS

| CN | 104166979 A | 11/2014 |
| CN | 105427277 A | 3/2016 |

OTHER PUBLICATIONS

International Search Report in PCT/CN2017/072203 dated May 31, 2017, 7 pages.
(Continued)

*Primary Examiner* — Michelle M Entezari
(74) *Attorney, Agent, or Firm* — Metis IP LLC

(57) ABSTRACT

The present application relates to a method for acquiring maximum principal strain or a maximum principal stress status of a vessel wall. The method includes: acquiring first vessel data of a first time phase corresponding to a vessel; acquiring second vessel data of a second time phase corresponding to the vessel; generating, based on the first vessel data, a first vessel model relating to the first time phase, generating a second vessel model relating to the second time phase based on the second vessel data; determining a region of interest in the first vessel model; determining the corresponding region of interest in the second vessel model; determining a reference point in the region of interest of the first vessel model; determining the corresponding reference point in the region of interest of the second vessel model; determining a displacement of the reference point from the first vessel model to the second vessel model; and deter-
(Continued)

mining a maximum principal strain or a maximum principal stress at the reference point based on the displacement of the reference point.

20 Claims, 14 Drawing Sheets

Related U.S. Application Data continuation of application No. PCT/CN2017/072203, filed on Jan. 23, 2017.

(51) Int. Cl.

| | | |
|---|---|---|
| G06T 7/149 | (2017.01) | |
| A61B 6/00 | (2006.01) | |
| A61B 5/02 | (2006.01) | |
| G06T 7/12 | (2017.01) | |
| G06T 7/13 | (2017.01) | |
| A61B 5/00 | (2006.01) | |
| A61B 6/03 | (2006.01) | |
| A61B 8/00 | (2006.01) | |
| G06T 7/60 | (2017.01) | |
| A61B 8/08 | (2006.01) | |
| A61B 5/055 | (2006.01) | |
| G06T 15/08 | (2011.01) | |

(52) U.S. Cl.
CPC ............ *A61B 5/743* (2013.01); *A61B 5/7405* (2013.01); *A61B 5/748* (2013.01); *A61B 6/032* (2013.01); *A61B 6/037* (2013.01); *A61B 6/463* (2013.01); *A61B 6/469* (2013.01); *A61B 6/5235* (2013.01); *A61B 8/463* (2013.01); *A61B 8/469* (2013.01); *G06T 7/12* (2017.01); *G06T 7/13* (2017.01); *G06T 7/149* (2017.01); *G06T 7/60* (2013.01); *G06T 7/97* (2017.01); *G06T 17/00* (2013.01); *A61B 5/055* (2013.01); *A61B 6/504* (2013.01); *A61B 6/5217* (2013.01); *A61B 8/0891* (2013.01); *A61B 8/485* (2013.01); *A61B 8/5223* (2013.01); *G06T 15/08* (2013.01); *G06T 2207/20021* (2013.01); *G06T 2207/30101* (2013.01); *G06T 2207/30104* (2013.01); *G06T 2207/30172* (2013.01); *G06T 2210/41* (2013.01)

(56) References Cited

U.S. PATENT DOCUMENTS

| | | | |
|---|---|---|---|
| 8,439,839 B2 | 5/2013 | Kadokura et al. | |
| 8,487,933 B2 | 7/2013 | Song et al. | |
| 8,892,188 B2* | 11/2014 | Buelow | G06T 7/12 |
| | | | 600/425 |
| 9,585,630 B2 | 3/2017 | Hyuga | |
| 10,210,614 B2* | 2/2019 | Wang | A61B 5/7225 |
| 10,653,394 B2 | 5/2020 | Friedrich et al. | |
| 2002/0183599 A1 | 12/2002 | Castellanos | |
| 2004/0082846 A1 | 4/2004 | Johnson et al. | |
| 2005/0249391 A1 | 11/2005 | Kimmel et al. | |
| 2006/0009837 A1 | 1/2006 | Burgermeister et al. | |
| 2006/0079772 A1* | 4/2006 | Ichikawa | G06T 7/66 |
| | | | 600/437 |
| 2007/0071324 A1* | 3/2007 | Thakur | H04N 1/00795 |
| | | | 382/199 |
| 2007/0282202 A1 | 12/2007 | Maurice et al. | |
| 2008/0181481 A1 | 7/2008 | Hong et al. | |
| 2008/0205722 A1* | 8/2008 | Schaefer | G06T 7/11 |
| | | | 382/128 |
| 2009/0185731 A1* | 7/2009 | Ray | G06T 7/12 |
| | | | 382/131 |
| 2009/0322749 A1* | 12/2009 | Kassab | G06T 7/66 |
| | | | 345/424 |
| 2010/0312113 A1 | 12/2010 | Ogasawara et al. | |
| 2012/0302878 A1 | 11/2012 | Liu et al. | |
| 2013/0116739 A1 | 5/2013 | Brada et al. | |
| 2014/0316758 A1 | 10/2014 | Yagi et al. | |
| 2014/0355850 A1* | 12/2014 | Kelm | G06T 7/12 |
| | | | 382/128 |
| 2014/0364739 A1* | 12/2014 | Liu | A61B 6/504 |
| | | | 600/407 |
| 2015/0049083 A1 | 2/2015 | Bidne et al. | |
| 2015/0127316 A1 | 5/2015 | Avisar | |
| 2015/0235360 A1 | 8/2015 | Zheng et al. | |
| 2016/0027182 A1* | 1/2016 | Oh | A61B 6/461 |
| | | | 382/131 |
| 2016/0058304 A1* | 3/2016 | Emblem | A61B 5/4848 |
| | | | 600/420 |
| 2016/0180052 A1 | 6/2016 | Godenschwager et al. | |
| 2016/0196645 A1 | 7/2016 | Ohayon et al. | |
| 2017/0084027 A1 | 3/2017 | Mintz | |
| 2017/0109496 A1 | 4/2017 | Hisada et al. | |
| 2017/0209059 A1 | 7/2017 | Nabutovsky et al. | |
| 2018/0005372 A1 | 1/2018 | Wang et al. | |
| 2018/0116521 A1 | 5/2018 | Kar et al. | |
| 2019/0380593 A1* | 12/2019 | Bouwman | A61B 6/465 |
| 2020/0390342 A1* | 12/2020 | Adiyoso | A61B 5/02028 |
| 2021/0298706 A1* | 9/2021 | Tu | G06T 11/206 |

OTHER PUBLICATIONS

Written Opinion in PCT/CN2017/072203 dated May 31, 2017, 8 pages.

Wang, Hongjian, IVUS-Based 2D/3D Biomechanical Model Analysis for Coronary Plaque Progression, Wan Fang Academic Joural Database (Academic Edition), 2017, 72 pages.

P. D. Richardson et al., influence of Plaque Configuration and Stress Distribution on Fissuring of Coronary Atherosclerotic Plaques, The Lancet, 334(8669): 941-944, 1989.

Howard M. Loree et al., Effects of Fibrous Cap Thickness on Peak Circumferential Stress in Model Atherosclerotic Vessels, Circulation Research, 71(4): 850-858, 1992.

George C. Cheng et al., Distribution of Circumferential Stress in Ruptured and Stable Atherosclerotic Lesions, A Structural Analysis with Histopathological Correlation, Circulation, 87(4): 1179-1187, 1993.

Hayden Huang et al., The Impact of Calcification on the Biomechanical Stability of Atherosclerotic Plaques, Circulation, 103(8): 1051-1056, 2001.

Wang, Liang et al., IVUS-Based FSI Models for Human Coronary Plaque Progression Study: Components, Correlation and Predictive Analysis, Annals of Biomedical Engineering, 43(1): 107-121, 2015.

Tang, Dalin et al., Sites of Rupture in Human Atherosclerotic Carotid Plaques Are Associated with High Structural Stresses, An In Vivo MRI-Based 3D Fluid-Structure Interaction Study, Stroke, 40(10): 3258-3263, 2009.

Tang, Dalin et al., 3D MRI-Based Anisotropic FSI Models with Cyclic Bending for Human Coronary Atherosclerotic Plaque Mechanical Analysts, Journal of Biomechanical Engineering, 131(6), 2009, 27 pages.

Tang, Dalin et al., A Negative Correlation Between Human Carotid Atherosclerotic Plaque Progression and Plaque Wall Stress: In Vivo MRI-Based 2D/3D FSI Models, Journal of biomechanics, 41(4): 727-736, 2008.

Tang, Dalin et al., 3D MRI-Based Multicomponent FSI Models for Atherosclerotic Plaques, Annals of Biomedical Engineering, 32(7): 947-960, 2004.

S. Z. Zhao et al., Blood Flow and Vessel Mechanics in a Physiologically Realistic Model of a Human Carotid Arterial Bifurcation, Journal of Biomechanics, 33(8): 975-984, 2000.

Wang, Yousheng et al., A Method of Analyzing the Strain of Arterial Wall, 2009 International Forum on Information Technology and Applications, 2: 217-220, 2009.

Joan Carol Main et al., Non-invasive display of helical flow pattern in the great vessels using a unique greyscale approach. Velocity

(56) References Cited

OTHER PUBLICATIONS

Vectors of vessel walls to display motion refelected by the blood flow pattern using shear forces from the flow on an ultrasound system, 2006.

* cited by examiner

METHOD AND SYSTEM FOR ACQUIRING STATUS OF STRAIN AND STRESS OF A VESSEL WALL

CROSS-REFERENCE TO RELATED APPLICATIONS

This present application is a continuation application of U.S. patent application Ser. No. 15/638,626, filed on Jun. 30, 2017, which is a continuation of International Application No. PCT/CN2017/072203, filed on Jan. 23, 2017, designating the United States of America, the contents of each of which are hereby incorporated by reference.

TECHNICAL FIELD

The present disclosure generally relates to a method and system for acquiring the status of a vessel wall, and more particularly, to a method and system for reconstructing a vessel model and determining the strain and stress of the vessel wall based on multi-time phase image data.

BACKGROUND

Imaging plays a significant role in medical care. There are various types of imaging technologies, including Digital Subtraction Angiography (DSA), Magnetic Resonance Imaging (MRI), Magnetic Resonance Angiography (MRA), Computed tomography (CT), Computed Tomography Angiography (CTA), Ultrasound Scanning (US), Positron Emission Tomography (PET), Single-Photon Emission Computerized Tomography (SPECT), SPECT-MR, CT-PET, CE-SPECT, DSA-MR, PET-MR, PET-US, SPECT-US, TMS (transcranial magnetic stimulation)-MR, US-CT, US-MR, X Ray-CT, X Ray-PET, X Ray-US, or the like, or a combination thereof. According to the imaging technologies, a three dimensional model of a human organ or tissue may be reconstructed on a computer. For example, a vessel model may be reconstructed. Due to the difference of blood flow velocity in a vessel within a cardiac cycle, the stress on the vessel wall may vary. The inner stress on the vessel wall may also vary within a cardiac cycle. Research on the stress status on the vessel wall may help a doctor determine which part of the vessel has a potential risk of breaking. A three dimensional vessel model for a complete cardiac cycle may be reconstructed based on multi-time phase vessel image data. And the stress status of the vessel may be acquired based on the vessel model. This may be helpful in precise disease diagnosis and assisting treatment.

SUMMARY

In one aspect of the present disclosure, a method of acquiring maximum principal strain and/or maximum principal stress status of a vessel wall is provided. The method may include acquiring first vessel data of a first time phase corresponding to a vessel, acquiring second vessel data of a second time phase corresponding to the vessel, generating, based on the first vessel data, a first vessel model relating to the first time phase, generating, based on the second vessel data, a second vessel model relating to the second time phase, determining a region of interest in the first vessel model, determining the corresponding region of interest in the second vessel model, determining a reference point in the region of interest of the first vessel model, determining the corresponding reference point in the region of interest of the second vessel model, determining a displacement of the reference point from the first vessel model to the second vessel model, and determining a maximum principal strain and/or a maximum principal stress at the reference point based on the displacement of the reference point.

In another aspect of the present disclosure, a non-transitory computer readable medium is provided. The medium may include executable instructions. The instructions, executed by at least one processor, may cause the at least one processor to implement the method of acquiring maximum principal strain and/or maximum principal stress status of a vessel wall.

In another aspect of the present disclosure, a system for acquiring maximum principal strain and/or maximum principal stress status of a vessel wall is provided. The system may include at least a processor and the executable instructions.

In another aspect of the present disclosure, a system is provided. The system may include at least one processor and a storage used for storing instructions. The instructions, executed by the at least one processor, may cause the system to implement the method of acquiring maximum principal strain and/or maximum principal stress status of a vessel wall.

According to some embodiments of the present disclosure, the method of acquiring maximum principal strain and/or maximum principal stress status of a vessel wall may further include comparing the maximum principal strain and/or the maximum principal stress at the reference point with a reference value, determining a vessel status based on the comparison, and providing the vessel status to a user.

According to some embodiments of the present disclosure, assessment results of vessel status may be presented in at least one form of an image, a chart, text with a fixed format, or audio.

According to some embodiments of the present disclosure, the reference data may be stored in a storage device.

According to some embodiments of the present disclosure, the providing the vessel status to a user may include sending the vessel status to at least one user terminal of a user.

According to some embodiments of the present disclosure, the comparing the maximum principal strain and/or the maximum principal stress at the reference point with a reference value may include determining a characteristic of the maximum principal strain and/or maximum principal stress at the reference point, and comparing the characteristic with the reference value.

According to some embodiments of the present disclosure, the characteristic of the maximum principal strain and/or maximum principal stress at the reference point may include a maximal value of maximum principal strains and/or maximum principal stresses at the reference point at different time phases.

According to some embodiments of the present disclosure, the characteristic of the maximum principal strain and/or the maximum principal stress at the reference point includes an average value of maximum principal strains and/or maximum principal stresses at the reference point in different time phases.

According to some embodiments of the present disclosure, the determining a reference point in the region of interest of the first vessel model may include dividing the first vessel model into a plurality of vessel slices, extracting a contour of a vessel slice of the plurality of vessel slices, and determining the reference point based on the contour of the vessel slice.

According to some embodiments of the present disclosure, the dividing the first vessel model into a plurality of vessel slices may include determining a center line of the extracted vessel model, dividing the center line into a plurality of center line segments, and determining a vessel segment corresponding to a center line segment as a vessel slice.

According to some embodiments of the present disclosure, the determining the reference point based on the contour of the vessel slice may include determining a plurality of candidate reference points at a same distance interval on the contour of the vessel slice, and determining the reference point in the plurality of candidate reference points.

According to some embodiments of the present disclosure, the method of acquiring maximum principal strain and/or maximum principal stress status of a vessel wall may further include determining an initial point in the plurality of candidate reference points, and numbering the plurality of candidate reference points in a clockwise or counterclockwise sequence from the initial point.

According to some embodiments of the present disclosure, the first vessel model may include a cardiovascular model, including a coronary artery and a vein. And the determining a region of interest in the first vessel model may include automatically determining the coronary artery in the cardiovascular model.

According to some embodiments of the present disclosure, the determining a region of interest in the first vessel model may include determining two points along a center line of the first vessel, and extracting a vessel segment between the two points.

According to some embodiments of the present disclosure, the determining a displacement of the reference point from the first vessel model to the second vessel model may include determining a displacement of the reference point between a first time phase and a second time phase immediately following the first time phase.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
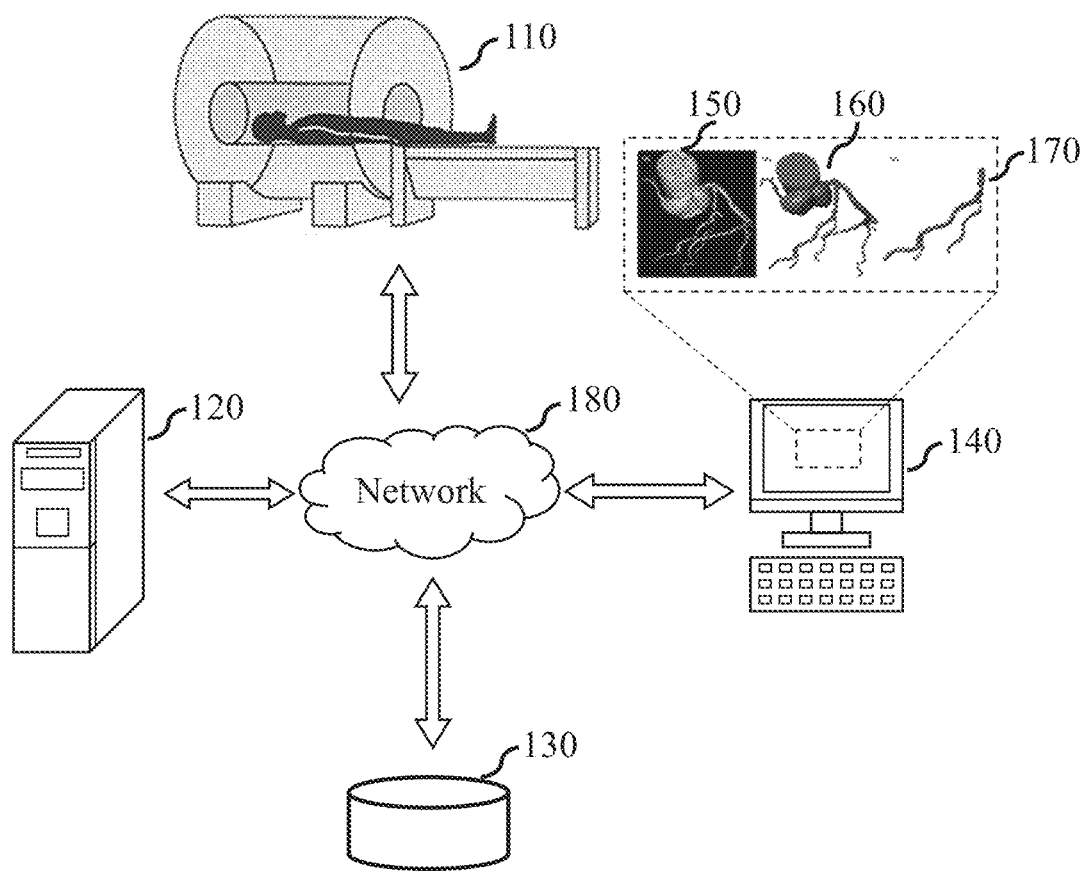
FIG. 1A and FIG. 1B illustrates schematic diagrams of a vessel status analysis system according to some embodiments of the present disclosure.

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

As used in the disclosure and the appended claims, the singular forms "a," "an," and "the" include plural referents unless the content clearly dictates otherwise. It will be further understood that the terms "comprises," "comprising," "includes," and/or "including" if used in the disclosure, specify the presence of stated steps and elements, but do not preclude the presence or addition of one or more other steps and elements.

Some modules of the system may be referred to in various ways according to some embodiments of the present disclosure, however, any number of different modules may be used and operated in a client terminal and/or a server. These modules are intended to be illustrative, not intended to limit the scope of the present disclosure. Different modules may be used in different aspects of the system and method.

According to some embodiments of the present disclosure, flow charts are used to illustrate the operations performed by a data processing system. It is to be expressly understood, the operations above or below may or do not be implemented in order. Conversely, the operations may be performed in inverted order, or simultaneously. Besides, one or more other operations may be added to the flowcharts, or one or more operations may be omitted from the flowchart.

In the process of image processing, "image segmentation," "image extraction," and "image classification" may each mean selecting an image that satisfies a specific condition from a large region and may be used interchangeably. According to some embodiments of the present disclosure, an imaging system may include one or more formats. The formats may include but are not limited to digital subtraction angiography (DSA), magnetic resonance imaging (MRI), magnetic resonance angiography (MRA), computed tomography (CT), computed tomography angiography (CTA), ultrasonic scanning (US), positron emission tomography (PET), single photon mission computed tomography (SPECT), SPECT-MR, CT-PET, CE-SPECT, DSA-MR, PET-MR, PET-US, SPECT-US, TMS-MR, US-CT, US-MR, X-ray-CT, X-ray-PET, X-ray-US, video-CT, video-US, or the like, or any combination thereof. In some embodiments, a subject of image scanning may include an organ, a body, an object, an injured section, a tumor, or the like, or any combination thereof. In some embodiments, a subject of image scanning may include a brain, a thorax, an abdomen, an organ, a bone, a vessel, or the like, or any combination thereof. In some embodiments, a subject of image scanning may include blood vessels of one or more tissues. In some embodiments, the image may include a 2-dimensional image and/or a 3-diemnsional image. A smallest distinguishable element of the 2-dimensional image may be a pixel. A smallest distinguishable element of the 3-dimensional image may be a voxel. The 3-dimensional image may include a series of 2-dimensional slices and/or 2-dimensional layers.

A process of image segmentation may be performed based on features corresponding to the pixels (or voxels) of an image. In some embodiments, the features corresponding to the pixels (or voxels) may include texture, grayscale, average grayscale, signal strength, color saturation, contrast, brightness, or the like, or any combination thereof. In some embodiments, a spatial position feature corresponding to the pixels (or voxels) may be used in the process of image segmentation.

It should be noted that the above description of the service system based on a location is provided for the purpose of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications do not depart from the spirit and scope of this disclosure.

FIG. 1A illustrates a schematic diagram of a vessel status analysis system 100 according to some embodiments of the present disclosure. The vessel status analysis system 100 may include a data collection device 110, a processing device 120, a storage device 130, and a communication device 140. The data collection device 110, the processing device 120, the storage device 130, and the communication device 140 may communicate with each other via a network 180.

The data collection device 110 may be configured to collect data. The data may include image data, object's features, etc. In some embodiments, the data collecting device 110 may include an imaging device. The imaging device may collect the image data. The imaging device may be a magnetic resonance imaging (MRI) device, a computed tomography (CT) device, a positron emission computed tomography (PET) device, a b-scan ultrasonography device, an ultrasonic diagnostic device, a thermal texture mapping (TTM) device, a medical electronic endoscope (MEE) device, or the like, or any combination thereof. The image data may include images or data of a blood vessel, a tissue, or an organ of an object. In some embodiments, the data collection device may include an object feature collection device. The object feature collection device may collect object features such as heart rate, heart rhythm, blood pressure, blood velocity, blood viscosity, cardiac output, myocardial mass, vascular flow resistance, and/or other object features associated with blood vessels, tissues or organs. In some embodiments, the object feature collection device may obtain age, height, weight, gender, or other features of the object. In some embodiments, the image data and the object features may be multi-time phase data. For example, the multi-time phase data may include data obtained from a same or similar position of an object at different time points or time phases. In some embodiments, the object feature collection device may be integrated in the imaging device so that the image data and the object's features may be collected simultaneously. In some embodiments, the data collection device 110 may send the collected data to the processing device 120, the storage device 130, and/or the communication device 140 via the network 180.

The processing device 120 may process data. The data may be collected by the data collection device 110. The data may also be obtained from the storage device 130, the communication device 140 (e.g., input data of a user), or from a cloud or an external device via the network 180. In some embodiments, the data may include image data, object's features data, user input, etc. The processing of the data may include selecting a region of interest from the image data. The region of interest may be selected solely by the processing device 120, or selected based on user input. In some embodiments, the region of interest may include a blood vessel, a tissue, an organ, etc. For example, the region of interest may be an artery, such as a coronary artery, an abdominal artery, a brain artery, a lower extremity artery, etc. The processing device 120 may further segment the region of interest. The technique of image segmentation may include a technique based on edges (e.g., a Perwitt operator, a Sobel operator, a gradient operator, a Kirch operator, etc.), a technique based on regions (e.g., a region growing technique, a threshold technique, a clustering technique, etc.), or other techniques based on fuzzy sets, a neural network, etc.

The processing device 120 may reconstruct a model that corresponds to the region of interest. The model may be selected based on the object's features, features of the region of interest, etc. For example, if selecting the coronary artery as the region of interest, the processing device 120 may segment an image that includes a coronary artery to extract an image of the coronary artery. The processing 120 may reconstruct the model according to the object features, general features of the coronary artery, image features of the coronary artery, etc. The reconstructed model may correspond to a vascular shape or a blood flow shape of the coronary artery. After reconstructing the model of the region of interest, the processing device 120 may preform analysis and computation based on the model.

In some embodiments, the processing device 120 may obtain data at multiple time phases. For example, the processing device 120 may obtain images of the coronary artery of an object at five different time phases. In such a situation, the processing device 120 may reconstruct models corresponding to regions of interest (e.g., an entire coronary artery, a branch of the coronary artery, a cross section of a blood entrance of the coronary artery, etc.) at different time phases respectively. The processing device 120 may then analyze and compute the models in sequence. In some embodiments, the processing device 120 may generate grids or meshes (also referred to as grid process or grid division) on the models at different time phases. The processing device 120 may correlate the grid processed models with each other to reduce computation load and improve computational accuracy. Techniques of correlating and grid processing may be found elsewhere in the present disclosure in, for example, FIG. 6 and FIG. 11, and their corresponding descriptions. In some embodiments, the analysis and computation result may include a physical state and a coefficient/ parameter of a blood vessel, a tissue, or an organ. For example, a result of analysis and computation of the model of the coronary artery may include a hemodynamic parameter such as blood velocity, blood pressure, wall stress of the blood vessel, wall shear stress (WSS) of the blood vessel, fractional flow reserve (FFR), coronary flow reserve (CFR), or the like, or any combination thereof. In some embodiments, the processing device 120 may generate a relationship between the physical state and/or the coefficient/parameter and time phase (e.g., changes of hemodynamic parameter with time). In some embodiments, the relationship may be generated based on the results of analysis and computation at different time phases. The relationship may be expressed as a curve or a table. The processing device 120 may obtain physical states and/or coefficients/parameters of the regions of interest at any time phase based on the curve or the table.

In some embodiments, the processing device 120 may denoise or smooth obtained data or a processing result. In some embodiments, the processing device 120 may send the obtained data or the processing result to the storage device 130 for storing, or the communication device 140 for displaying. The processing result may be an intermediate result generated in the process (e.g., a model of a region of interest), or a final result of the process (e.g., an analyzed and computed hemodynamic parameter, etc.). In some embodiments, the processing device 120 may be one or more processing units or devices, such as central processing units (CPUs), graphics processing units (GPUs), digital signal processors (DSPs), systems on a chip (SoC), microcontroller units (MCUs), etc. In some embodiments, the processing device 120 may be a specially designed processing unit or device with specific functions. The processing device 120 may be local, or remote with respect to the data collection device 110.

The storage device 130 may store data or information. The data or information may include data obtained by the data collection device 110, processing results or control instructions generated by the processing device 120, user input received by the communication device 140, etc. The storage device 130 may be one or more storage mediums with read/write functions. The storage device 130 may include but not limited to a static random access memory (SRAM, a random-access memory (RAM), a read-only memory (ROM), a hard disk, a flash memory, etc. In some embodiments, the storage device 130 may be a remote storage device, such as a cloud disk, etc.

The communication device 140 may be configured to receive, send, and/or display data or information. The received data or information may include the data obtained by the data collection device 110, the processing results generated by the processing device 120, the data stored by the storage device 130, etc. For example, the data or information displayed by the communication device 140 may include an actual image 150 of a cardiovascular obtained by the data collection device 110, a cardiovascular model 160 reconstructed by the processing device 120 based on the actual image 150, a coronary artery model extracted from the cardiovascular model 160 by the processing device 120, etc. The formats of display may include but is not limited to a 2-dimensional or 3-dimensional medical image, a geometric model and its grid processed result, a vector diagram (e.g., a velocity vector), a contour map, a filled contour map (cloud chart), an XY scatter plot, a particle trajectory map, a simulated flow effect, or the like, or any combination thereof. As another example, the data or information sent by the communication device 140 may include input information of a user. The communication device 140 may receive one or more operating parameters of the processing device 120 input by the user, and send the operating parameters to the processing device 120.

In some embodiments, the communication device 140 may include a user interface. The user may provide a user input to the communication device 140 by specific interactive apparatuses such as a mouse, a keyboard, a touchpad, a microphone, etc. For example, the user may click on the model displayed by the communication device 140 and select a region of interest of the model. As another example, the user may select any position of the vascular model displayed by the communication device 140. The communication device 140 may then obtain a blood velocity, a blood pressure, a blood flow, etc. of that position from the processing device 120 and display them.

In some embodiments, the communication device 140 may be a device with displaying function, such as a screen. In some embodiments, the communication device 140 may have some or all functions of the processing device 120. For example, the communication device 140 may implement operations (e.g., smoothing, denoising, changing colors, etc.) to the results generated by the processing device 120. Merely by way of example, the operation of changing colors may include transforming a grayscale image to a color image, or transforming a color image to a grayscale image. In some embodiments, the communication device 140 and the processing device 120 may be an integrated device. The integrated device may implement functions of both the processing device 120 and the communication device 140. In some embodiments, the communication device 140 may include a desktop computer, a server, a mobile device, etc. The mobile device may include a laptop computer, a tablet computer, an iPad, a built-in device of a vehicle (e.g., a motor vehicle, a ship, an airplane), a wearable device, etc. In some embodiments, the communication device 140 may include or is connected to a display apparatus, a printer, a fax machine, etc.

The network 180 may be used for internal communication of the vessel status analysis system 100. The network 180 may also be configured to receive information from or send information to an external device outside the system 100. In some embodiments, the data collection device 110, the processing device 120, and the communication device 140 may be connected to the network 180 via a wired connection, a wireless connection, or a combination thereof. The network 180 may be a single network or a combination of networks. In some embodiments, the network 180 may include but is not limited to a local area network (LAN), a wide area network (WAN), a public network, a proprietary network, a wireless local area network (WLAN), a virtual network, an urban metropolitan area network, a public switched telephone network (PSTN), or the like, or any combination thereof. In some embodiments, the network 180 may include multiple network access points, such as a wired or wireless access point, a base station or network switched point, etc. Through these access points, any data source may be connected to the network 180 and transmit information via the network 180.

Figure 1B:
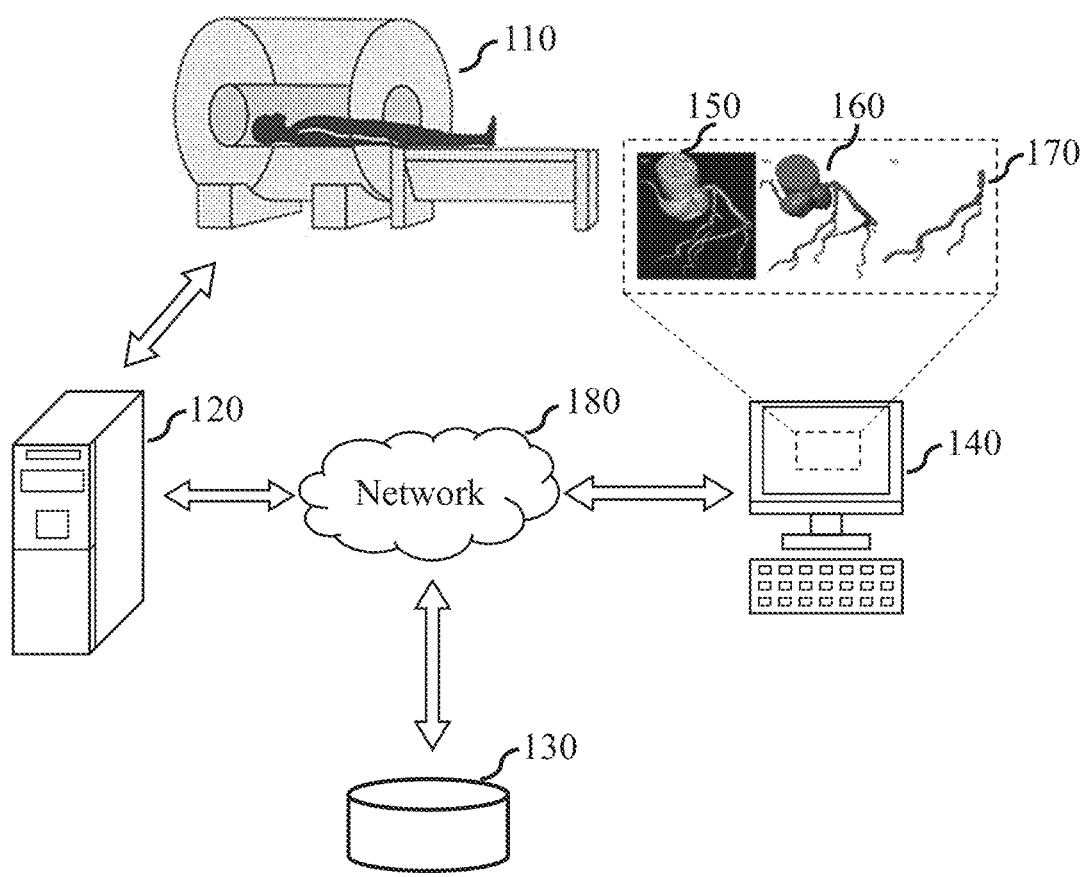

FIG. 1B illustrates another schematic diagram of a network environment including a vessel status analysis system 100 according to some embodiments of the present disclosure. FIG. 1B is similar to FIG. 1A. In FIG. 1B, the processing device 120 may be directly connected to the data connection device 110. The data connection device 110 are not directly connect to the network 180.

The above description of the present disclosure is provided for the purposes of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications do not depart the spirit and scope of this disclosure. For example, the data connection device 110, the processing device 120, and the communication device 140 may directly exchange information with each other without the network 180. As another example, the devices may exchange information by a removable storage device or another intermediate medium.

Figure 2A:
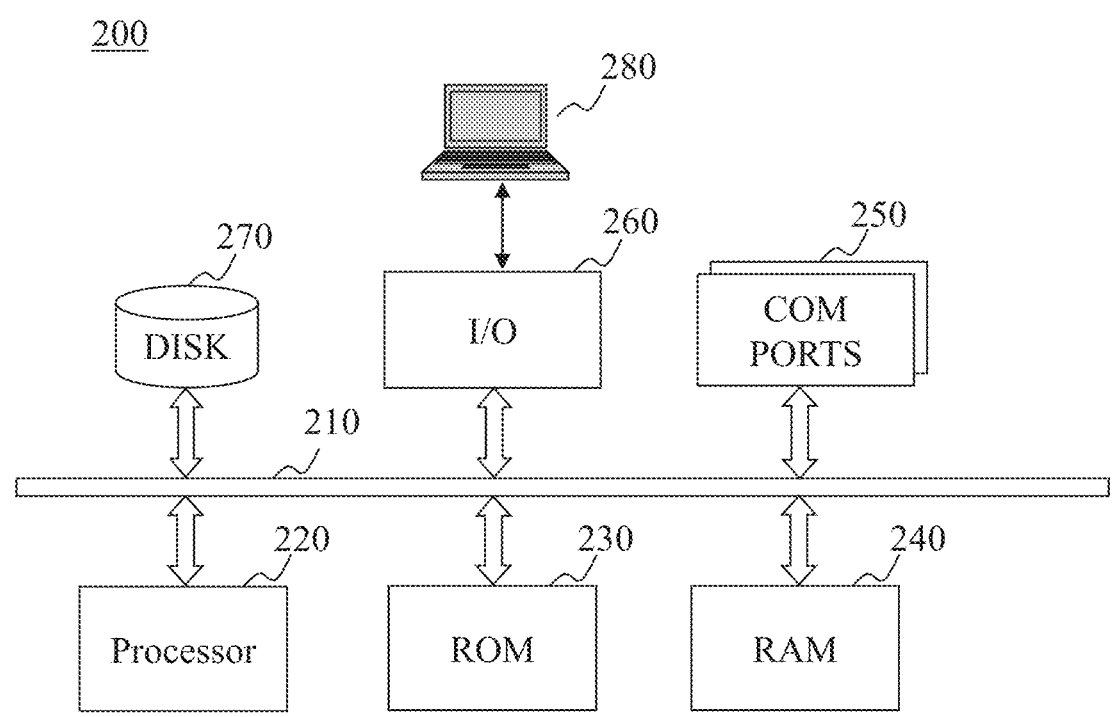
FIG. 2A illustrates a structure of a computing device that can implement a specific system according to some embodiments of the present disclosure.

FIG. 2A illustrates a structure of a computing device 200 that can implement a specific system according to some embodiments of the present disclosure. The computing device 200 may implement a specific system of the present disclosure. The specific system of the present disclosure may use a functional diagram to describe a hardware platform including a user interface. The computing device 200 may configured to implement one or more components, modules, units, sub-units (e.g., the processing device, the interactive device, etc.) of the blood flow condition analysis system 100. The one or more components, modules, units, sub-units (e.g., the processing device, the interactive device, etc.) of the blood flow condition analysis system 100 may be implemented by the computing device 200 by a hardware device, a software program, a firmware, or any combination thereof of the computing device 200. The computing device 200 may be a general purpose computing device, or a specific purpose computing device. The computing devices may be configured to implement the specific system of the present disclosure. For brevity, the FIG. 2 illustrates only one computing device. According to some embodiments, functions of processing and pushing information may be processing loads of a decentralized system implemented on a set of similar platforms in a distributed manner.

As showed in FIG. 2, the computing device 200 may include an internal communication bus 210, a processor 220, a read-only memory (ROM) 240, a random-access memory (RAM) 240, a communication port 250, an input/output component 260, a hard disk 270, a user interface 280, etc. The internal communication bus 210 may be configured to implement data communications between components of the computing device 200. The processor 220 may implement program instructions to complete one or more functions, components, modules, units, sub-units of the blood flow condition analysis system 100 disclosure in the present disclosure. The processor 220 may include one or more processors. The commination port 250 may be configured to implement data communications (e.g., via the network 180) between the computing device 200 and other parts (e.g., the data connection device 110) of the blood flow condition analysis system 100. The computing device 200 may include different forms of program storage unit and data storage unit, such as a hard disk 270, a read-only memory (ROM) 230, a random access memory (RAM) 240, various data files used by a computing device for processing or communication, a possible program instruction implemented by the processor 220. The input/output component 260 may support inputting/outputting data stream between the computing device 200 and other components (e.g., the user interface 280), and/or other components of the blood flow condition analysis system 100. The computing device 200 may send and receive information and data through the communication port 250 via the network 180.

Figure 2B:
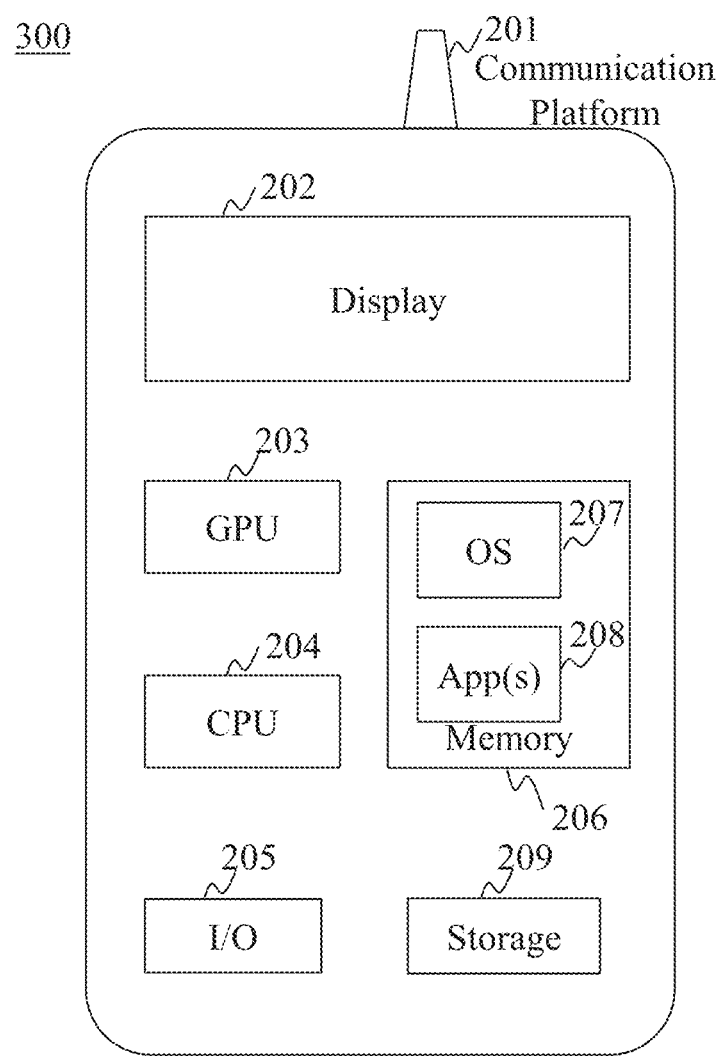
FIG. 2B illustrates a schematic diagram of a mobile device that can implement a specific system according to some embodiments of the present disclosure.

FIG. 2B illustrates a schematic diagram of a mobile device that can implement a specific system according to some embodiments of the present disclosure. In some embodiments, a user device that is configured to display information related to an interactive position may be a mobile device 300. The mobile device 300 may include a smart phone, a tablet computer, a music player, a portable game console, a GPS receiver, a wearable calculating device (e.g. glasses, watches, etc.), etc. The mobile device 300 may include one or more central processing units (CPUs) 204, one or more graphical processing units (GPUs) 203, a display 202, a memory 206, an antenna 201 (e.g. a wireless communication unit), a storage unit 209, and one or more input/output (I/O) devices 205. Moreover, the mobile device 300 may also include any other suitable component that includes but is not limited to a system bus or a controller (not shown in FIG. 3). As shown in FIG. 2B, a mobile operating system 207 (e.g. iOS, Android, Windows Phone, etc.) and one or more applications 208 may be loaded from the storage unit 209 to the memory 206 and implemented by the CPUs 204. The application 208 may include a browser or other mobile applications configured to receive and process information related to the images or blood flow condition analyses in the mobile device 300. The communication information related to the images or blood flow condition analyses between the user and the one or more components of the system 100 may be obtained through the I/O device 205, and provide the information to the processing device 120 and/or other modules or units of the system 100, e.g. the network 180.

Figure 3:
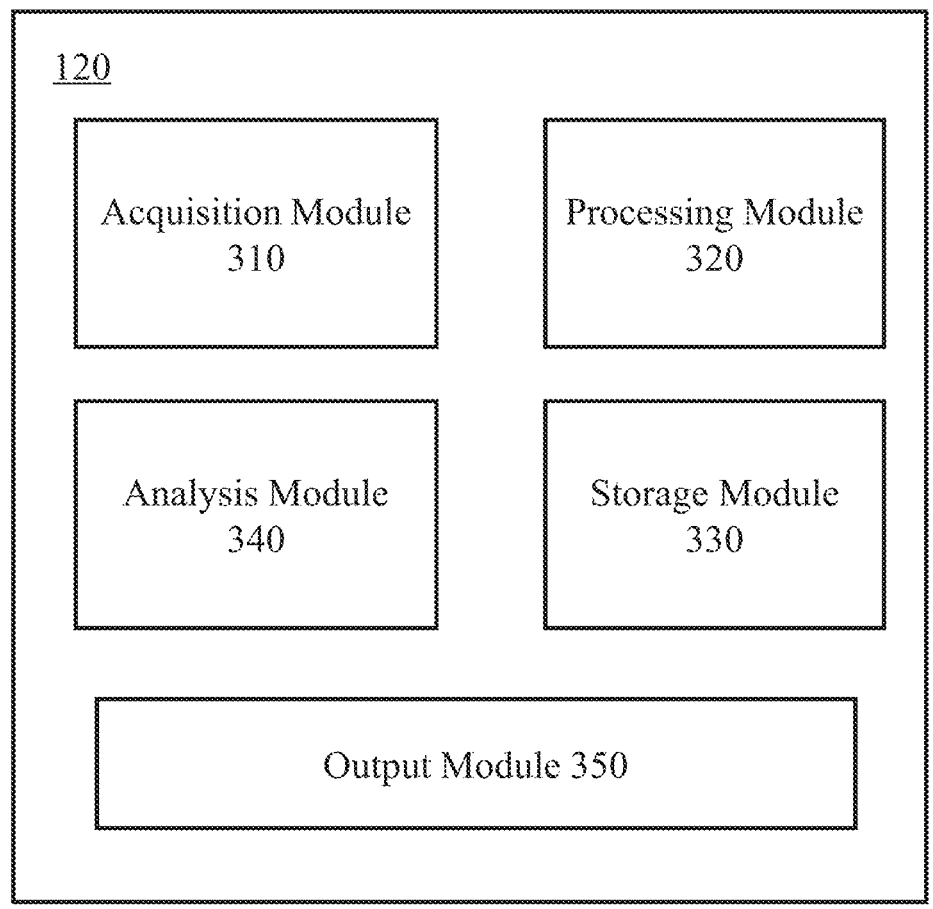
FIG. 3 illustrates a schematic diagram of an exemplary processing device according to some embodiments of the present disclosure.

FIG. 3 illustrates a schematic diagram of an exemplary processing device according to some embodiments of the present disclosure. The processing device 120 may include an acquisition module 310, a processing module 320, a storage module 330, an analysis module 340 and an output module 350.

The acquisition module 310 may receive image data, characteristic data of an object, or the like, from the data collection device 110 and/or the storage module 330. The image data may include images or data of vessels, tissues or organs of an object. The characteristic data of the object may include characteristic data relating to vessels, tissues or organs of an object such as heart rate, heart rhythm, blood pressure, blood flow velocity, blood viscosity, cardiac output, myocardiac mass, vascular resistance, or the like. The characteristic data of the object may also include age, height, weight, gender, or the like, of the object. In some embodiments, the image data and the characteristic data of the object may be data for multi-time phases. For example, the data of multi-time phases may be data obtained at different time points or time phases at a same or similar part of the object.

The processing module 320 may process data and generate a corresponding image according to the data. The data may be obtained from the acquisition module 310, the storage module 330, and/or other modules not shown in the figures. The data may be external data resource obtained via the network 180. The data processed by the processing module 320 may also relate to a specific part of the object, such as a brain, a heart, a vessel, a lung, a bronchus, or the like, or a combination thereof. In some embodiments, the processing module 320 may process data relating to a vessel. The processing module 320 may process the data based on multiple types of mode, including parameter selectable mode, automatic processing mode, program processing mode, function processing mode, or the like, or a combination thereof. In some embodiments, the user may select data needed to be processed. For example, the user may select data relating to a vessel at a specific location in the image to be processed. In some embodiments, the function processing mode may include preprocessing of vessel image data based on a histogram fitting, image data processing based on function transformation, image data processing based on weight computation, or the like, or a combination thereof. The processing of the image data may include image preprocessing, rough segmentation of the image, tracing of the image characteristic points, and/or image transform, or the like. The program processing mode may include selecting different programs to process the data at different periods according to different requirements. The function processing mode may include level set technique, gradient descent technique, exponential function transformation technique, histogram data expansion function fitting, or the like, or a combination thereof.

The storage module 330 may store data or information. The stored data or information may be in various forms such as a value, a signal, an image, information relating to the object, an instruction, an algorithm, a program, or the like, or a combination thereof. In some embodiments, the stored data may include a vessel image, parameters of the vessel image, processed data of the vessel image, programs and/or algorithms for processing the vessel image, etc.

The analysis module 340 may analyze data. In some embodiments, the analysis module 340 may analyze a result determined by the processing module 320. For example, the analysis module 340 may compare the determination result of the processing module 320 with a reference value. In some embodiments, the analysis module 340 may format the analysis result. For example, the analysis module 340 may convert the analysis result into a chart or a report.

The output module 350 may output the analysis result or computation data. For example, the output module 350 may send the analysis result or the computation data to the storage device 130 for storage, or the communication device 140 for display. The output module 350 may also present the analysis result or the computation data to the user in various forms such as voice, etc. The computation result may include an intermediate result, or a final result. Herein, the intermediate result may include a model of region of interest, or the like. The final result may include a parameter of a maximum principal strain and/or a maximum principal stress (also referred to as strain and/or stress) of a vascular wall generated by analysis or computation, a relation curve or a look-up table for the computation results and the time phases, etc.

Figure 4:
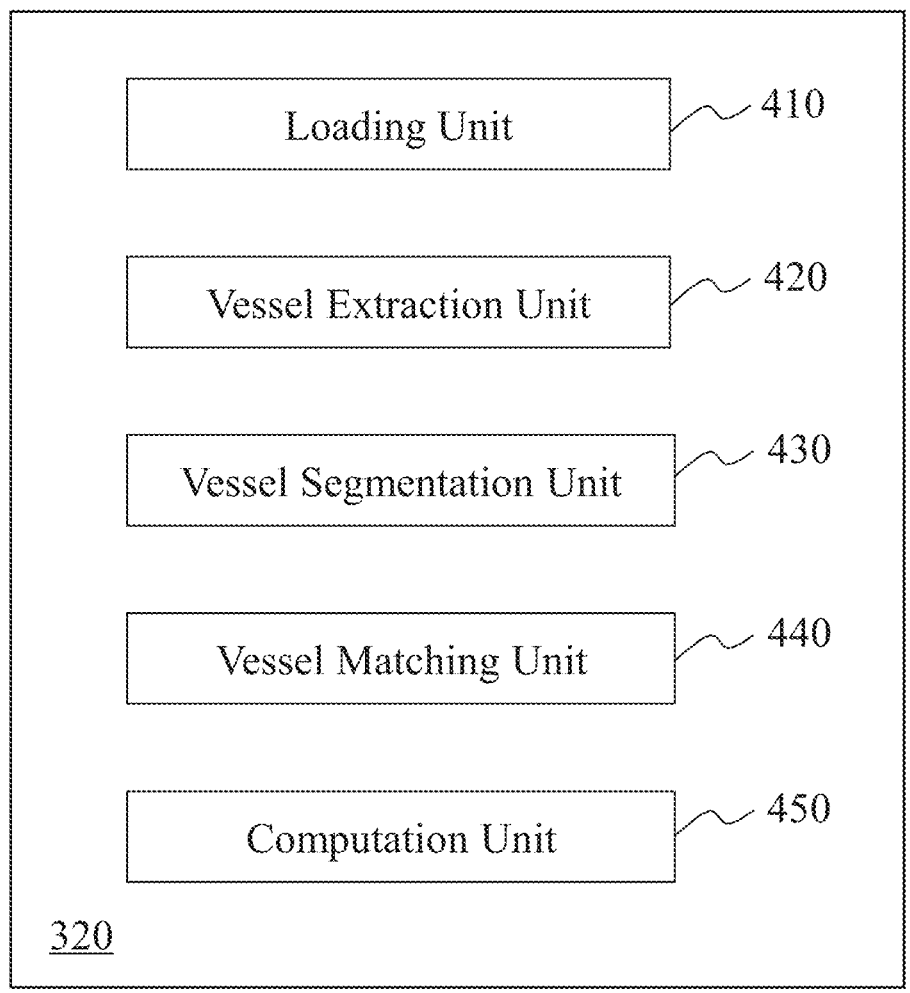
FIG. 4 illustrates a schematic diagram of an exemplary processing module 320 according to some embodiments of the present disclosure.

FIG. 4 illustrates a schematic diagram of an exemplary processing module 320 according to some embodiments of the present disclosure. The processing module 320 may include a data loading unit 410, a vessel extraction unit 420, a vessel segmentation unit 430, a vessel matching unit 440 and a computation unit 450. All the modules are interconnected directly or indirectly.

The data loading unit 410 may load vessel data to generate a vessel model. The vessel data may be received from the acquisition module 310 and/or the storage module 330. In some embodiments, the vessel data may be received from the acquisition module 310. The data from the acquisition module 310 may be obtained from the data collection device 110. For example, the data collection device 110 may generate a series of CT tomography images. The CT tomography images may be loaded into the data loading unit 410 via the acquisition module 310. In some embodiments, the vessel data may be received from the storage module 330. For example, a medical record of an object may be stored in the storage module 330. When an arteriography image of corresponding diagnosis included in the medical record is needed, the arteriography image may be directly acquired from the storage module 330 and sent to the data loading unit 410. The data loading unit 410 may load vessel image data into the processing module 320.

The vessel image data may include a series of vessel arteriography images, or electronic data associated with vessel structure. In some embodiments, the series of vessel arteriography images may include images of different cross sections of a part or all of a vessel. The number of the series of vessel arteriography images may be determined based on a processing ability of the data collection device 110 or an amount of information of the vessel stored in the storage module 330. For example, the data collection device 110 may be able to image x cross sections of the vessel. Then the number of the series of vessel arteriography images may be equal to or less than x. As another example, the medical records stored in the storage module 330 of the object may include y cross sections of the vessel. Then the number of the series of vessel arteriography images may be equal to or less than y. In some embodiments, the vessel image data may be electronic data. For example, the data collection device 110 may generate a simulated vessel model. The vessel model may include a plurality of voxels. Each of the voxels may correspond to a coordinate. A sum of all the coordinates of the voxels may be used to reconstruct a complete vessel model. The coordinate information of the voxels may be transmitted as electronic data and loaded into the processing module 320 by the data loading unit 410. The data volume of the electronic data may be determined based on resolution of the voxels. For example, if the vessel model is segmented into more voxels, then a larger volume of data may be generated.

The loaded vessel image data may include image data corresponding to a vessel status at a specific time phase, image data corresponding to the vessel status in multiple sets of different time phases, or dynamic image data of the vessel status within a specific time period. In some embodiments, the loaded vessel image data are image data corresponding to the vessel status in a specific time phase. For example, cardiac contraction and relaxation in a cardiac cycle may cause the status of a vessel to change. The specific time phase may include a time phase when the heart contracts to a largest degree, a time phase when the heart relaxes to a largest degree, or a random time phase when the heart contracts or relaxes. In some embodiments, the loaded vessel image data is image data corresponding to the states of the vessel in multiple sets of different time phases. For example, the multiple sets of different time phases may extend across a part of or an entire cardiac cycle. The part of the cardiac cycle may be a time period corresponding to the process of cardiac relaxation or a time period corresponding to the process of cardiac contraction. The image data corresponding to the states of the vessel in multiple sets of different time phases may indicate the status change of the vessel within a corresponding time period. The number of the multiple sets of different time phases may be determined based on an ability of the data collection device 110, or the processing ability of the data loading unit 410, or by the user. For example, the data collection device 110 may have a higher imaging resolution in the time domain. More sets of vessel images may be generated within a time period. As another example, the data loading unit 410 may have limited data processing capacity. The number of the multiple sets of different time phases may be limited by the processing capacity of the data loading unit 410. As another example, a research on the vessel status may need to achieve high precision. More sets of vessel data may be needed to reconstruct the status change of the vessel within the time period under examination. In some embodiments, the loaded vessel image data may be dynamic image data of the status of the vessel within a specific time period. For example, the data output result of the data collection device 110 may be a movie. The movie may show continuous changes of the vessel within the research time period at a specific frame rate.

The vessel data may be a vessel image enhanced by the angiography. In some embodiments, the image data outputted by the data collection device 110 may include a vessel, or any other tissues. The other tissues may include muscle tissue, skeleton, organs, etc. The vessel and the tissues may overlap. In order to exclude influence from the other tissues on the research of the vessel, the angiography may be performed on the image data outputted by the data collection device 110 to separate out the vessel.

The loaded vessel data may be used to generate a vessel model. The vessel model may be a three dimensional vessel model. If the loaded vessel data include multiple sets of vessel data of different time phases, multiple sets of three dimensional vessel models of different time phases may be generated corresponding to the multiple sets of vessel data of different time phases by the data loading unit 410. The vessel model may be generated based on a series of vessel cross-section images, or electronic data of a vessel. In some embodiments, the loaded vessel data may be a series of vessel cross-section images. The series of vessel cross-section images may be combined and fitted to generate an intact vessel model in space based on the contours of the vessel in each of the vessel cross-section image and corresponding coordinates of the vessel cross-section images. In some embodiments, the vessel model may be generated based on electronic data of vessel. For example, the loaded vessel data may include coordinates of different voxels of the vessel that are outputted by the data collection device 110. The data loading unit 410 may arrange the voxels of the vessel in space based on the coordinates and further fit the arranged voxels to generate the vessel model. In some embodiments, the vessel model may be a dynamic three-dimensional image. For example, the vessel data provided by the data collection device 110 may include information regarding the continuous change of a voxel coordinate of the vessel within a time period. The vessel model may be generated by fitting coordinates of each of the voxels and continuously displaying the fitting results. In this way, a continuous three-dimensional video model with specific frames may be generated.

The vessel extraction unit 420 may extract a local vessel in the vessel model. The local vessel may include a cluster of vessels, a vessel or a part of a vessel. In some embodiments, the arteriography may be performed on a cardiac vessel. The cardiac vessel may include a coronary artery and a cardiac vein. A doctor may assess that the coronary artery or cardiac vein may contain some lesion according to different symptoms of an object. A segmentation of the coronary artery and the cardiac vein in the vessel model may be preferred for diagnosis purposes. As another example, in some embodiments, a vessel with abnormity may be preliminarily determined by the doctor based on the data provided by the data collection device 110. After the vessel model is generated, the vessel extraction unit 420 may extract the abnormal vessel for specific analysis. As another example, in some embodiments, a local vessel in the vessel model is obviously abnormal. The local vessel may be extracted to perform further analysis.

The vessel segmentation unit 430 may segment a vessel into a plurality of vessel parts. In some embodiments, the vessel model or the extracted part of the vessel model may be segmented into a plurality of vessel units (also referred as vessel slices) with smaller sizes before further analysis. Each of the vessel slices may be analyzed independently. The analysis result of each of the vessel slices may then be integrated to generate an intact analysis result of the researched vessel. In some embodiments, the vessel segmentation unit 430 may segment the vessel into a plurality of surfaces along a direction parallel to the extension direction of the vessel. In some embodiments, the vessel segmentation unit 430 may segment the vessel into a plurality of hollow cylinders along a direction perpendicular to a center line of the vessel. The center line of the vessel may be a virtual line parallel to the extension direction of vessel and located inside the vessel. The hollow part of the hollow cylinders may allow blood to flow through. Segmentation sizes of the hollow cylinders may be homogeneous or heterogeneous. In some embodiments, the vessel to be analyzed may be homogeneously segmented into a plurality of segments. In some embodiments, some parts of interest of the vessel may be segmented more precisely. For example, the parts of interest of the vessel may be segmented into smaller pieces or thinner vessel slices. However, other parts that are of less interest may be segmented relatively roughly. For example, these parts of the vessel may be divided into larger pieces or thicker vessel slices.

The vessel matching unit 440 may match a same vessel segment at different time phases. In some embodiments, multiple sets of vessel data at different time phases of a same vessel segment may be loaded into the processing module 320. After a vessel model is generated, the status of a same vessel segment of the vessel at the different time phases may need to be analyzed. The vessel models of different time phases may be matched to determine locations of the same vessel segment in vessel models of different time phases. The matching may include matching a vessel segment or matching points on a vessel. For example, the voxels of a vessel may be numbered when a vessel model is generated. Regions corresponding to voxels with same numbering may be designated as matched regions.

The computation unit 450 may be used to determine the status change of a vessel. The status change may include displacement of a point on the vessel, change of strain and/or stress of a vessel within a time period, distribution of strain and/or stress of a vessel in a specific time phase, or the like, or a combination thereof. In some embodiments, the computation unit 450 may determine the status change of each vessel slice. Then the computation unit 450 may integrate the results of the status change according to the segmentation algorithms of the vessel slices to generate status information of the vessel. In some embodiments, the computation unit 450 may determine a pair of vessel models to determine the status change of the two vessels. The computation may include determining the status change of reference points on vessel models of two adjacent time phases. For example, the status change of the reference points on the first vessel model of a first time phase and the second vessel model of a second time phase may be determined. And the status change of the reference points on the second vessel model of the second time phase and the third vessel model of a third time phase may be determined. The computation unit 450 may integrate the results of status change of the vessel according to the order of time phases in order to generate a continuous status change of the vessel. For example, the status change of reference points between the first time phase and the second time phase may be combined with the status change of reference points between the second time phase and the third time phase. In this way, a dynamic status change of the reference points during the time period from the first time phase to the third time phase may be determined. Thus, the dynamic change during the cardiac cycle of each reference point on the vessel model may be determined in a similar way.

It should be noted that the above description of the processing module 320 is provided for the purpose of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications do not depart the spirit and scope of this disclosure. For example, in some embodiments, the vessel model generation function of the data loading unit 410 may be implemented by a vessel model generation subunit to generate a vessel model. In some embodiments, the vessel extraction unit 420 and the vessel segmentation unit 430 may be combined into a unit to obtain vessel slices.

Figure 5:
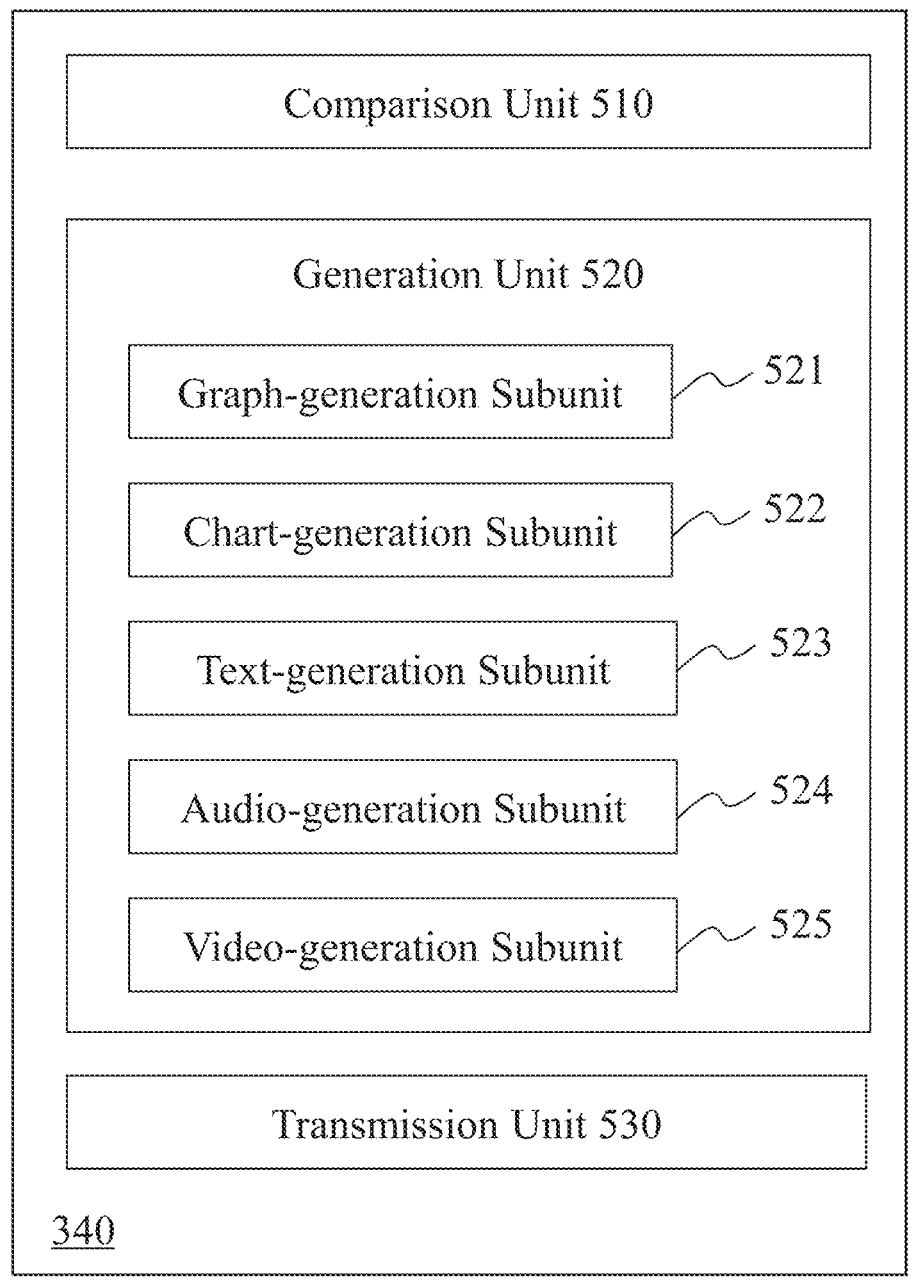
FIG. 5 illustrates a schematic diagram of an exemplary analysis module 340 according to some embodiments of the present disclosure.

FIG. 5 illustrates a schematic diagram of an exemplary analysis module 340 according to some embodiments of the present disclosure. The analysis module 340 may include a comparison unit 510, a generation unit 520, and a transmission unit 530. All the units are interconnected directly or indirectly.

The comparison unit 510 may compare the computation result of vessel status from the computation unit 450 with a reference result to generate a comparison result. The reference result may be data stored in the storage module 330, data stored in the network 180, or data provided by a user. In some embodiments, the reference result and the comparison result of the vessel status may be stored in a chart. For example, if the vessel status refers to vessel stress, the reference result may be a correlation chart of vessel stress range and corresponding risk level. The risk level may include normal level, early warning level, dangerous level, extremely dangerous level, etc. In some embodiments, the user may provide the correlation according to clinical experience. In some embodiments, the comparison may be comparing computation results of vessel status collected at different times. For example, the computation results of vessel status collected in the morning, afternoon, and evening of a day of an object may be compared by the comparison unit 510 to determine the change of vessel status of the object within a day. This may assist a doctor to assess when the vessel of the object is relatively vulnerable during a day.

The generation unit 520 may present the results generated by the comparison unit 510 in various presentation forms. The presentation forms may include a statistical graph, a statistical chart, a text with fixed format, an audio, or the like, or a combination thereof. The results may be presented to the user via the communication device 140. The generation unit 520 may include a graph-generation subunit 521, a chart-generation subunit 522, a text-generation subunit 523, an audio-generation subunit 524, and a video-generation subunit 525. All the subunits are interconnected directly or indirectly.

The graph-generation subunit 521 may generate a series of statistical graphs, color and/or gray vessel model images, or the like. The statistical graphs may include a curve graph, a line graph, a pie graph, a histogram, etc. For example, the statistical graphs may include a curve graph about stress variation of a vessel in a cardiac cycle. The color and/or gray vessel model images may indicate the distribution of parameters of vessel status by using different depths of color and/or gray scale. For example, a darker color may be used to indicate a region with higher stress on a vessel. The region may be considered to have a risk of breaking.

The chart-generation subunit 522 may generate a series of data comparison charts. For example, in some embodiments, items in the columns of a chart may be serial numbers of vessels or vessel slices. Items in the rows of the chart may be types of status parameters of vessels or vessel slices. The types of status parameters may include displacement, strain, stress, or the like. Reference values corresponding to the types of status parameters may also be included in the chart. Early warning results regarding the vessels or the vessel slices may be generated according to the reference values. The early warning results may include "normal," "early warning," "dangerous," "extremely dangerous," or the like.

The text-generation subunit 523 may convert the results generated by the comparison unit 510 or the computation unit 450 into text description with a fixed format. The text description with a fixed format may be a predesigned text. The text may be filled or modified in some fixed parts of the text according to the computation results and the comparison results. For example, the predesigned text may be "In a cardiac cycle, for . . . on the No . . . vessel, the largest strain is . . . , the largest stress is . . . , and the largest reference stress is . . . . Thus, the risk of breaking for the . . . on the vessel is low/high/extremely high".

The audio-generation subunit 524 may generate an audio report and/or a corresponding early warning sound according to the comparison results. In some embodiments, the audio report may be generated by adding the comparison results or the computation results into corresponding parts of a predetermined audio record. For example, the above text description may be recorded as an audio template. The audio template may be used to report the comparison results or the computation results at a specific time. In some embodiments, the early warning audio alert may be generated according to the early warning results in the comparison results. For example, if the early warning result is "dangerous" or "extremely dangerous," the communication device 140 may generate a beeping sound with different frequencies to alert the user.

The video-generation subunit 525 may generate an animation or a video according to the results generated by the comparison unit 510 or the computation unit 450. For example, the video-generation subunit 525 may convert the computation results generated by the computation unit 450 into an animation. The animation may include status change of the vessel, blood flow, or blood condition within a time period (e.g., one or more cardiac cycles, etc.). In some embodiments, a video report may include audio, text, an icon, or the like, or a combination thereof. For example, an animation that presents the status change of the vessel, blood flow, or blood condition within a time period (e.g., one or more cardiac cycles, etc.) may be combined with an audio explanation or text description to provide one or more parameters of the vessel, blood flow, or blood condition in different time phases. The parameter may include blood pressure, stress, or the like.

The transmission unit 530 may transmit the generated results in different presentation forms to the output module 350 that may further transmits the data to different user terminals, or directly to different user terminals. In some embodiments, results generated by the generation unit 520 and computation results generated by the computation unit 450 may be transmitted to a user terminal via the network 180. The user terminal may include a computer, a phone, a display device, a printer, a facsimile machine, or the like. The results may be transmitted to multiple user terminals simultaneously. In some embodiments, the multiple user terminals may be local or remote to the data collection device 110 or the processing device 120. For example, an object may be diagnosed by different doctors. The result of vessel status of the object may be simultaneously transmitted to the object, a family member of the object, a guardian of the object, different doctors of the object, or the like.

It should be noted that the above description of the analysis module 340 is provided for the purpose of illustration, and not intended to limit the scope of the present disclosure. For persons having ordinary skills in the art, modules may be combined in various ways or connected with other modules as sub-systems. Various variations and modifications may be conducted under the teaching of the present disclosure. However, those variations and modifications do not depart the spirit and scope of this disclosure. For example, in some embodiments, one or more subunits in the generation unit 520 may be omitted.

Figure 6:
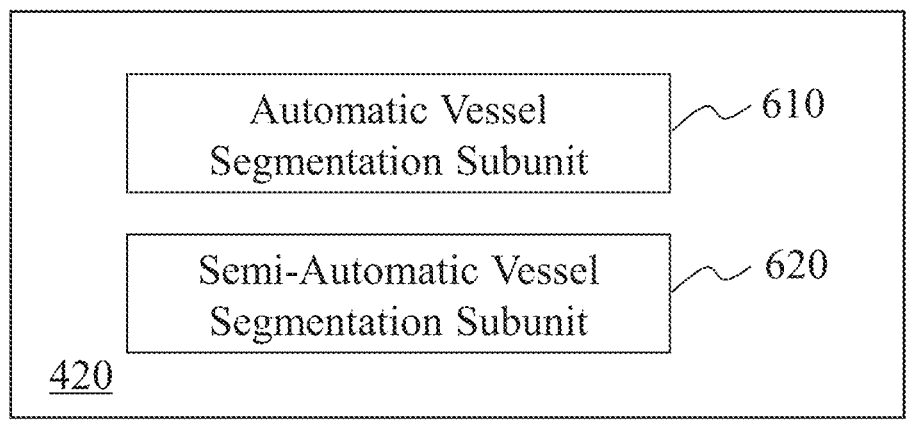
FIG. 6 illustrates a schematic diagram of an exemplary vessel extraction unit according to some embodiments of the present disclosure.

FIG. 6 illustrates a schematic diagram of an exemplary vessel extraction unit 420 according to some embodiments of the present disclosure. The vessel extraction unit 420 may include an automatic vessel segmentation subunit 610 and a semi-automatic vessel segmentation subunit 620. The segmentation may refer to segmenting a vessel model. The segmentation may include distinguishing vessels and other tissues of a body, segmenting a type of vessel (e.g., coronary) and other types of vessels, segmenting a specific part (e.g., vessel segments close to the heart) of a vessel and other parts of the vessel, or the like. The vessel segmentation may be performed based on one or more types of algorithms. The vessel segmentation algorithms may include threshold algorithm, region growing algorithm, energy function-based algorithm, level set algorithm, area segmentation and/or combination, edge tracing segmentation algorithm, statistical pattern recognition algorithm, mean clustering segmentation algorithm, model method, deformable model-based segmentation algorithm, artificial neural network algorithm, minimal path segmentation algorithm, tracing method, rule-based segmentation algorithm, coupling surface segmentation algorithm, or the like, or a combination thereof.

The automatic vessel segmentation subunit 610 may automatically segment a vessel model. In some embodiments, the automatic segmentation algorithms may be pre-stored in a computing device (e.g., the computing device shown in FIG. 2A) in advance. For example, if each single vessel in a vessel cluster needs to be independently analyzed in order to analyze a type of vessel, the single vessels in the vessel model may be segmented after the vessel model is generated. In some embodiments, the automatic segmentation algorithms may be determined based on the position of the vessel. For example, in a diagnosis of heart disease, a doctor may need to know the stress distribution on the cardiac coronary artery of the object. Thus, the coronary artery and cardiac vein in the vessel model may be automatically segmented after the cardiac vessel model is generated. In some embodiments, the automatic segmentation algorithms may be determined based on the purpose of the diagnosis. For example, a doctor may need to know the distribution of capillary in some disease diagnosis. Thus, vessel segments with relatively larger diameters and vessel segments with relatively smaller diameters in the generated vessel model may be segmented. The automatic segmentation algorithms may be stored in the storage module 330 and may be invoked by a user via the communication device 140 when needed. The automatic segmentation algorithms may also be upgraded via the network 180. For example, the manufacturer of the device may periodically or non-periodically optimize the vessel segmentation algorithms, or provide new vessel segmentation algorithms. The manufacture of the device may also provide corresponding data package for users to download and update the vessel segmentation algorithms.

The semi-automatic vessel segmentation subunit 620 may segment a vessel partly based on instructions of a user. In some embodiments, a doctor may need to perform a personalized vessel segmentation according to the special condition of an object. In such a situation, automatic vessel segmentation may be improper. The doctor may perform segmentation manually according to the specific symptom of the object after a vessel model is generated. For example, the doctor may select some regions with a high possibility of getting disease in the vessel model via the communication device 140 and segment the regions. The selection may refer to designating a region or a vessel segment on the vessel model. The designating a vessel segment may refer to manually selecting two points on a single vessel and segment the portion of the vessel between the two points. The manual segmentation may be implemented based on automatic segmentation. For example, the coronary may be firstly segmented by the automatic vessel segmentation subunit 610 in diagnosis of cardiac coronary. Then a doctor may further segment a potentially pathological region on the segmented coronary. In some embodiments, there may be some errors in automatically segmented vessels due to incompetence of the automatic segmentation algorithm or insufficient computation capacity of the computing device. The errors may influence a doctor's diagnosis. In such a situation, manual segmentation may be used to modify the vessels generated by automatic segmentation. For example, if some cardiac veins are still connected to the coronary after automatic segmentation of cardiac coronary, the remaining cardiac veins may be manually segmented from the coronary via the semi-automatic vessel segmentation subunit 620. As another example, a threshold for determining capillary automatically may be set as a relatively broad range in order to avoid computation errors of a computing device in analysis or diagnosis of an organ or tissue capillaries. The computation errors may lead to missing some capillaries. After the automatic segmentation, there may be still some vessels with relatively large diameters left. Then the vessels with relatively large diameters may be segmented through the semi-automatic vessel segmentation subunit 620.

Figure 7:
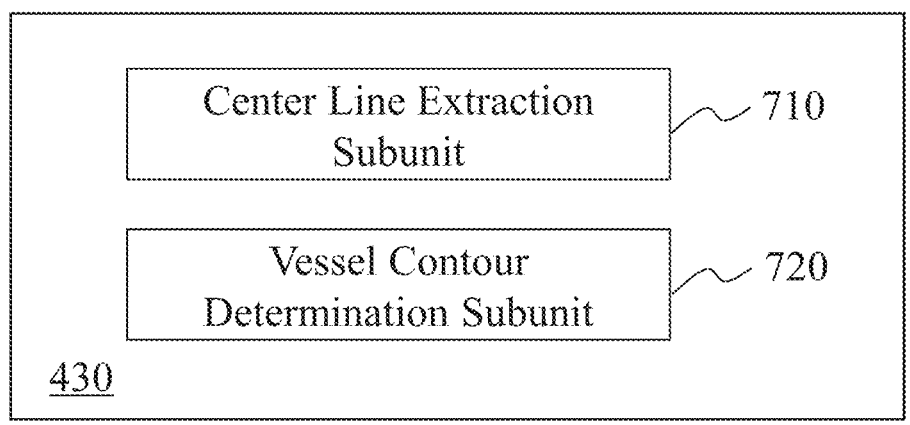
FIG. 7 illustrates a schematic diagram of an exemplary vessel segmentation unit according to some embodiments of the present disclosure.

FIG. 7 illustrates a schematic diagram of an exemplary vessel segmentation unit 430 according to some embodiments of the present disclosure. The vessel segmentation unit 430 may include a center line extraction subunit 710 and a vessel contour determination subunit 720. The vessel segmentation may refer to segmenting a vessel into a plurality of units that can be processed by numerical analysis using a segmentation method. For example, the vessel may be segmented into a plurality of parts according to the number of voxels in the vessel model. As another example, the vessel may be segmented into a plurality of vessel segments by segmenting the vessel along the direction perpendicular to the center line of the vessel. As another example, a vessel wall with a certain surface area may be segmented from the vessel at a certain size.

The center line extraction subunit 710 may extract the center line of a vessel. In some embodiments, the center line of the vessel may refer to a hypothetical line that is parallel to the extension direction of vessel and located inside the vessel. The center line of the vessel may include a set of one or more pixels or voxels in the vessel. The vessel may include a set of pixels or voxels on the boundary of the vessel or within the boundary of the vessel. In some embodiments, the center line of the vessel may include a set of pixels or voxels at or close to the center of the vessel, or a line consisting of the set. In some embodiments, the center line of the vessel may include one or more end points of the vessel. The center line of the vessel may be a route between the end points. In some embodiments, the center line of the vessel may be determined by firstly segmenting the vessel into a plurality of vessel segments perpendicular to the extension direction the vessel. Then a center point in the center of each of the plurality of vessel segments may be determined. The center point may be determined based on the condition that the statistical variance of distances between the center point and the vessel wall is the minimal. The center points of the plurality of vessel segments may be fitted using a curve. In some embodiments, exemplary methods for extracting the center line of the vessel may be found in PCT/CN2016/097294 filed on Aug. 30, 2016, the contents of which are hereby incorporated by reference. After the center line of the vessel is determined, the vessel may be evenly segmented into a plurality of center line segments. Each of the center line segments may correspond to a segment of the vessel wall. The segment of the vessel wall may be designated as vessel slices outputted by the vessel segmentation unit 430. If the lengths of the segmented center line segments are short enough, the thickness of the vessel slices parallel to the extension direction of the vessel may be ignored. The vessel slice may be a ring corresponding to the cross section of the vessel.

The vessel contour determination subunit 720 may perform discretization on the vessel slices. The vessel contour determination subunit 720 may determine contours of the vessel slices. Since the vessel walls of the vessel slices have thickness, the contours of the vessel walls may be approximate to contours of the vessel inner walls, contours of the vessel outer walls, or other closed curves representing the ring structure of the vessel slices. In some embodiments, the contour line may be processed by discretization for the purpose of analysis because the contour of the vessel slice is a continuous curve. For example, reference points may be set on the contour line of the vessel slices every a certain distance. The distribution of the reference points may be homogeneous or heterogeneous. For example, in some embodiments, the research on the cardiac vessel may focus on the condition of the vessel close to the side of the cardiac muscle. In such a situation, more reference points may be set on the side of the vessel slice close to the cardiac muscle. And relatively fewer reference points may be set at the other side of the vessel slice. In some embodiments, the reference points may be marked in order to match same vessel segments in vessel models of different time phases. For example, a point on a vessel slice may be marked as "M–n." This means that the point is the $n^{th}$ reference point on the $M^{th}$ vessel slice. When analyzing the status of the same vessel segments in vessel models of different time phases, reference points with the same marks may be matched. The reference points may be marked according to the space coordinates of the vessel model. For example, the reference points may be marked according to distances from each of the reference points to the original point of the coordinate system. The reference points may also be marked according to the types of the vessels. For example, a reference point closest to the cardiac muscle may be set as the initial reference point in a research on vessels covering the surface of the cardiac muscle. And the reference points may be marked in a clockwise or counterclockwise order.

Figure 8:
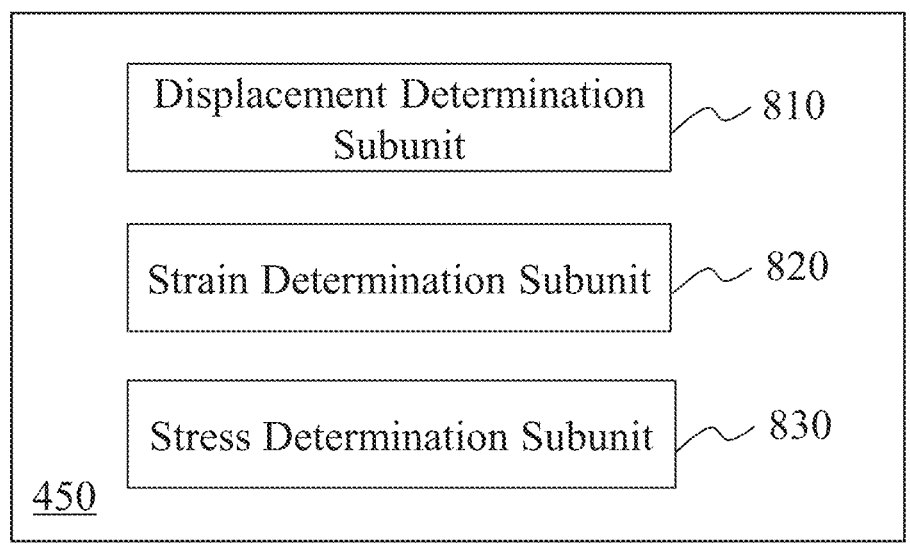
FIG. 8 illustrates a schematic diagram of an exemplary computation unit according to some embodiments of the present disclosure.

FIG. 8 illustrates a schematic diagram of an exemplary computation unit 450 according to some embodiments of the present disclosure. The computation unit 450 may include a displacement determination subunit 810, a strain determination subunit 820 and a stress determination subunit 830. All the subunits may be independent or interconnected. For example, the strain may be determined based on the determined displacement. The stress may be determined based on the determined strain.

The displacement determination subunit 810 may determine displacements of the reference points. The displacements may include displacements of a reference point corresponding to different vessel models in a same model space. In some embodiments, the displacement may be a relative displacement. For example, the coordinate of a reference point in the first vessel model of a first time phase is designated as A. The coordinate of the corresponding reference point in the second vessel model of a second time phase is designated as B. Then the relative displacement of the reference point from the first vessel model of the first time phase to the second vessel model of the second time phase may be a space vector directing from A to B. In this way, displacements of the plurality of reference points in the first vessel model of the first time phase and the second vessel model of the second time phase may be determined. The computation results of the displacements may be stored in the storage module 330. The strain determination subunit 820 may determine strain corresponding to the reference points. In some embodiments, the strain may be determined based on the determined displacements of corresponding reference points in different time phases. For example, the strain may be determined according to the Green strain tensor, or the like. The results of the strain may be stored in the storage module 330. The stress determination subunit 830 may determine stress corresponding to the reference points. In some embodiments, the stress may be determined according to the relationship between the strain and the stress. For example, the elastic modulus of the vessel may be determined based on a lookup table. The stress may be determined based on the elastic modulus and the strain. The results of the stress may be stored in the storage module 330

Figure 9:
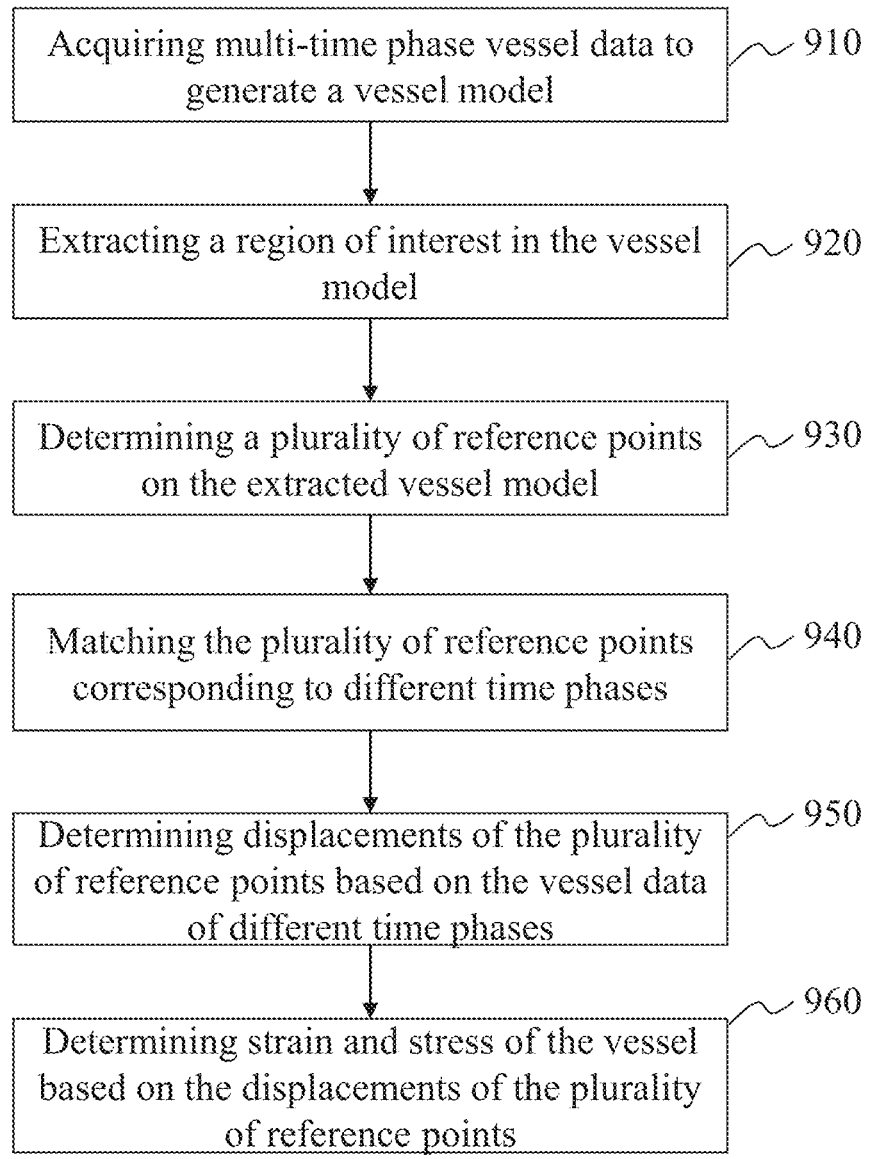
FIG. 9 is a flowchart illustrating an exemplary process for acquiring the strain and stress of a vessel according to some embodiments of the present disclosure.

FIG. 9 is a flowchart illustrating an exemplary process for acquiring strain and stress of a vessel according to some embodiments of the present disclosure. The process may include acquiring multi-time phase vessel data to generate a vessel model 910, extracting a region of interest in the vessel model 920, determining a plurality of reference points on the extracted vessel model 930, matching the plurality of reference points corresponding to different time phases 940, determining displacements of the plurality of reference points based on the vessel data of different time phases 950 and determining strain and stress of the vessel based on the displacements of the plurality of reference points 960.

In 910, multi-time phase vessel data may be acquired to generate a vessel model. In some embodiments, the process of acquiring vessel data of multi-time phases may be performed by the data loading unit 410. The vessel data may include vessel image data received by the data loading unit 410. The vessel data may include vessel angiography images or electronic data. Detailed description about types of vessel data may refer to the description of the data loading unit 410. In some embodiments, the loaded vessel image data may be image data corresponding to the vessel status in multiple sets of different time phases. For example, the multiple sets of different time phases may include a part of or the entire cardiac cycle. The part of the cardiac cycle may be a time period corresponding to cardiac relaxation or a time period corresponding to cardiac contraction. The image data corresponding to the vessel status in multiple sets of different time phases may indicate the status change of the vessel within the corresponding time period. The number of the multiple sets of different time phases may be determined based on the device performance, or by the user. For example, the number may be lower than or equal to the maximum number of sets of vessel data that the data collection device 110 is able to collect or generate within a cardiac cycle. As another example, the number of sets may be determined based on a judgment of a doctor based on the difficulty of disease diagnosis. The more difficult the disease diagnosis is, the more sets may be needed. The vessel data may be an image enhanced by the angiography. In some embodiments, image data outputted by the data collection device 110 may include a vessel, or any other tissues. The other tissues may include muscle tissue, skeleton, organs, or the like. The vessel and the other tissues may overlap in an image. In order to exclude influence from the other tissues on the research of the vessel, the angiography may be performed on the image data outputted by the data collection device 110 to distinguish the vessel. In some embodiments, the process of generating a vessel model may be performed by the data loading unit 410. The vessel model may be a three dimensional vessel model. If the loaded vessel data is vessel data of multi-time phases, vessel models corresponding to the vessel data of multi-time phases may be generated by the data loading unit 410. Techniques for generating a vessel model may be found in the description of the data loading unit 410.

In 920, a region of interest in the vessel model may be extracted. In some embodiments, operation 920 may be performed by the vessel extraction unit 420. In some embodiments, the region of interest may be determined based on the symptom of the object. For example, if the object has angina when his heart contracts, the doctor may determine that the cardiac coronary vessel of the object may have a condition. In such a situation, the coronary vessel of the object may be determined as the region of interest. As another example, if the object feels uncomfortable in a part of the body including a lot of capillaries, the doctor may determine that the part of the body including a lot of capillaries may have a condition. In such a situation, the part of the body including a lot of capillaries may be determined as the region of interest. The region of interest may be determined by the user via the communication device 140. The process for extracting the region of interest in the vessel model may include vessel segmentation performed by the vessel extraction unit 420. The extracting may be automatic and/or semi-automatic. The methods about vessel segmentation may be found in the descriptions of the vessel extraction unit 420, the automatic vessel segmentation subunit 610, and the semi-automatic vessel segmentation subunit 620. The results of the extraction process may include acquiring a vessel or a segment of a vessel.

In 930, a plurality of reference points on the extracted vessel model may be determined. In some embodiments, operation 930 may be performed by the vessel segmentation unit 430 and the vessel contour determination subunit 720. In order to analyze the change of vessel models of different time phases, change of corresponding points in multi-time phases may be analyzed. In some embodiments, the extracted vessel model may be firstly segmented. Exemplary segmentation techniques may be found in the descriptions about the vessel segmentation unit 430. In some embodiments, the vessel may be segmented or sliced along the direction perpendicular to the center line of the vessel to obtain a series of vessel segments. If the number of the vessel segments or slices are many enough, the thickness of the vessel segments along the direction of the center line of the vessel may be omitted. In some embodiments, contours of the vessel segments may be extracted by the vessel contour determination subunit 720. Then reference points may be determined on the contours. Techniques for determining reference points may be found in the description of the vessel contour determination subunit 720.

In 940, reference points corresponding to different time phases may be determined. In some embodiments, operation 940 may be performed by the vessel matching unit 440. The reference points corresponding to different time phases may be compared with each other after being matched. For example, a reference point in the first vessel model of a first time phase does not be compared with other reference points in the second vessel model of a second time phase. Exemplary techniques for matching reference points may be found in the description of the vessel matching unit 440.

In 950, displacements of reference points may be determined based on the vessel data of different time phases. In some embodiments, operation 950 may be performed by the displacement determination subunit 810. In some embodiments, the displacements of reference points may refer to relative displacements of sequential time phases. For example, a point on the vessel may correspond to a reference point A1 in the vessel model of a first time phase, a reference point A2 in the vessel model of a second time phase, and a reference point A3 in the vessel model of a third time phase. The displacements of the reference points may include the displacement from the reference point A1 to the reference point A2, and the displacement from the reference point A2 to the reference point A3. The displacement from the reference point A1 to the reference point A3 are not be included. In this way, continuous displacement change information of the point in vessel models of multi-time phases may be obtained. Exemplary techniques about determining the displacement may refer to the description of the displacement determination subunit 810.

In 960, strain and stress of the vessel may be determined based on the displacements of reference points. In some embodiments, operation 960 may be performed by the strain determination subunit 820 and the stress determination subunit 830. A continuous strain change and a corresponding stress change may be determined based on the continuous displacement change information generated in 950 and the relation between the displacement, the strain and the stress. Exemplary techniques for determining the strain and the stress of the vessel may be found in the description of the strain determination subunit 820 and the stress determination subunit 830.

It should be noted that the above description of acquiring strain and stress of a vessel is provided for the purpose of illustration, and not intended to limit the scope of the present disclosure. For persons having ordinary skills in the art, modules may be combined in various ways, or connected with other modules as sub-systems. Various variations and modifications may be conducted under the teaching of the present disclosure. However, those variations and modifications do not depart the spirit and scope of this disclosure. For example, operation 920 may be omitted. In some embodiments, reference points may be determined on the intact vessel model. This may cause increase of computation amount, but operations 930, 940, 950 and 960 may still be performed.

Figure 10:
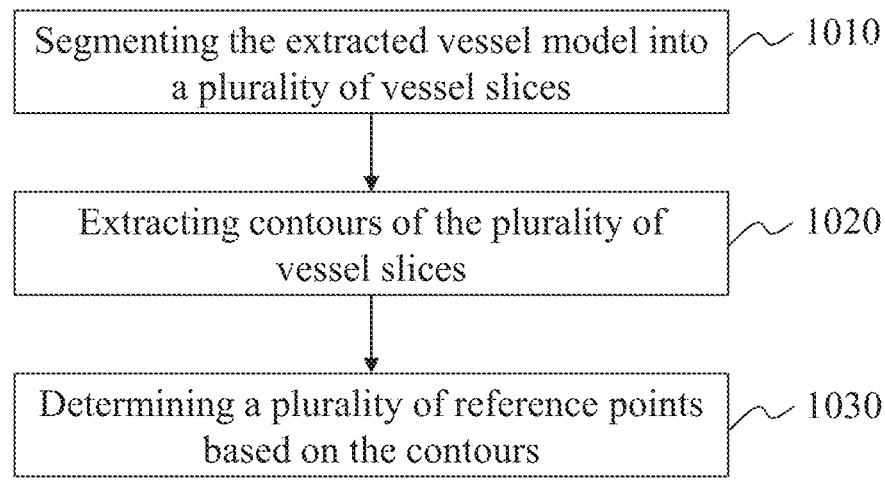
FIG. 10 is a flowchart illustrating an exemplary process for determining reference points on an extracted vessel model according to some embodiments of the present disclosure.

FIG. 10 is a flowchart illustrating an exemplary process for determining reference points on an extracted vessel model according to some embodiments of the present disclosure. The process may include segmenting the extracted vessel model into a plurality of vessel slices 1010, extracting contours of the plurality of vessel slices 1020, and determining a plurality of reference points based on the contours 1030.

In 1010, the extracted vessel model may be segmented into a plurality of vessel slices. In some embodiments, operation 1010 may be performed by the vessel segmentation unit 430. In some embodiments, the segmentation may include segmenting the vessel model into a plurality of vessel segments along the direction perpendicular to the extension direction of the vessel. Exemplary methods of segmentation may refer to the description of the vessel segmentation unit 430.

In 1020, contours of the vessel slices may be extracted. In some embodiments, operation 1020 may be performed by the vessel contour determination subunit 720. The contours of the vessel slices may be contours of the inner wall of the vessel, contours of the external wall of the vessel, or other closed curves representing the ring structure of the vessel slices. Exemplary techniques for determining the contours of the vessel slices may be found in the description of the vessel contour determination subunit 720.

In 1030, a plurality of reference points may be determined based on the contours of the vessel. In some embodiments, operation 1030 may be performed by the vessel contour determination subunit 720. In some embodiments, determining reference points may refer to performing discretization on the contours of the vessel. Exemplary techniques for performing discretization may refer to the description of the vessel contour determination subunit 720. In some embodiments, the vessel under research is a vessel on the surface of the cardiac muscle. Then the reference point closest to the cardiac muscle may be set as the initial reference point. And the other reference points may be marked in a clockwise or counterclockwise order.

Figure 11:
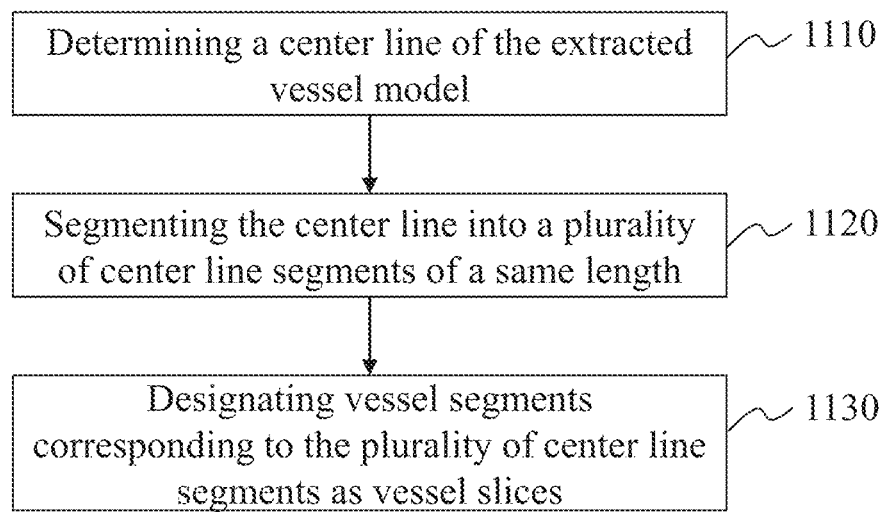
FIG. 11 is a flowchart illustrating an exemplary process for segmenting an extracted vessel model into a plurality of vessel slices according to some embodiments of the present disclosure.

FIG. 11 is a flowchart illustrating an exemplary process for segmenting an extracted vessel model into a plurality of vessel slices according to some embodiments of the present disclosure. The process may include determining a center line of the extracted vessel model 1110, segmenting the center line into a plurality of center line segments of a same length 1120, and designating vessel segments corresponding to the plurality of center line segments as vessel slices 1130. In some embodiments, the process may be performed by the vessel segmentation unit 430.

In 1110, the center line of the extracted vessel model may be determined. In some embodiments, operation 1110 may be performed by the center line extraction subunit 710. In some embodiments, the center line of the vessel may be a virtual line parallel to the extension direction of vessel and located inside the vessel. Exemplary techniques for determining the center line of the vessel may be found in the description of the center line extraction subunit 710.

In 1120, the center line may be segmented into a plurality of center line segments of a same length. In some embodiments, operation 1120 may be performed by the center line extraction subunit 710. The number of the segmented center line segments of a same length may be determined by the processing ability of computation devices or desired precision of the processing results. In some embodiments, segmenting the center line may refer to segmenting the extracted vessel model into a plurality of units, performing analysis on the respective segmented unit, and combining the analysis results. If the number of the units is too many, the computation amount may be increased and the processing time may be extended. Correspondingly, the precision of the processing results after combination may be improved. The user may select a number of the units needed to be segmented according to practical clinical requirements. For example, an object under emergency treatment in an operating room is in urgent need of diagnosis result of the vessel status. The doctor may hope to obtain the processing results as soon as possible. In such situation, the number of the units to be segmented may be decreased. As another example, the illness of an object cannot be determined after multiple times of diagnosis. The doctor may hope to obtain more precise processing results. In such a situation, the number of the units to be segmented may be increased.

In 1130, vessel segments corresponding to the plurality of center line segments may be designated as vessel slices. In some embodiments, operation 1130 may be performed by the center line extraction subunit 710. After the center line segments of the vessel is segmented, the range of the vessel wall may be determined based on the segmented center line segments. In some embodiments, a plane perpendicular to a center line segment may be used to scan the center line segment from an end to the other end. The vessel wall involved by the plane may be determined as the vessel wall corresponding to the center line segment. If the lengths of the segmented center lines are short enough, the thickness of the vessel slices parallel to the extension direction of the vessel may be omitted. The vessel slice may be a ring structure corresponding to the cross section of the vessel.

Figure 12:
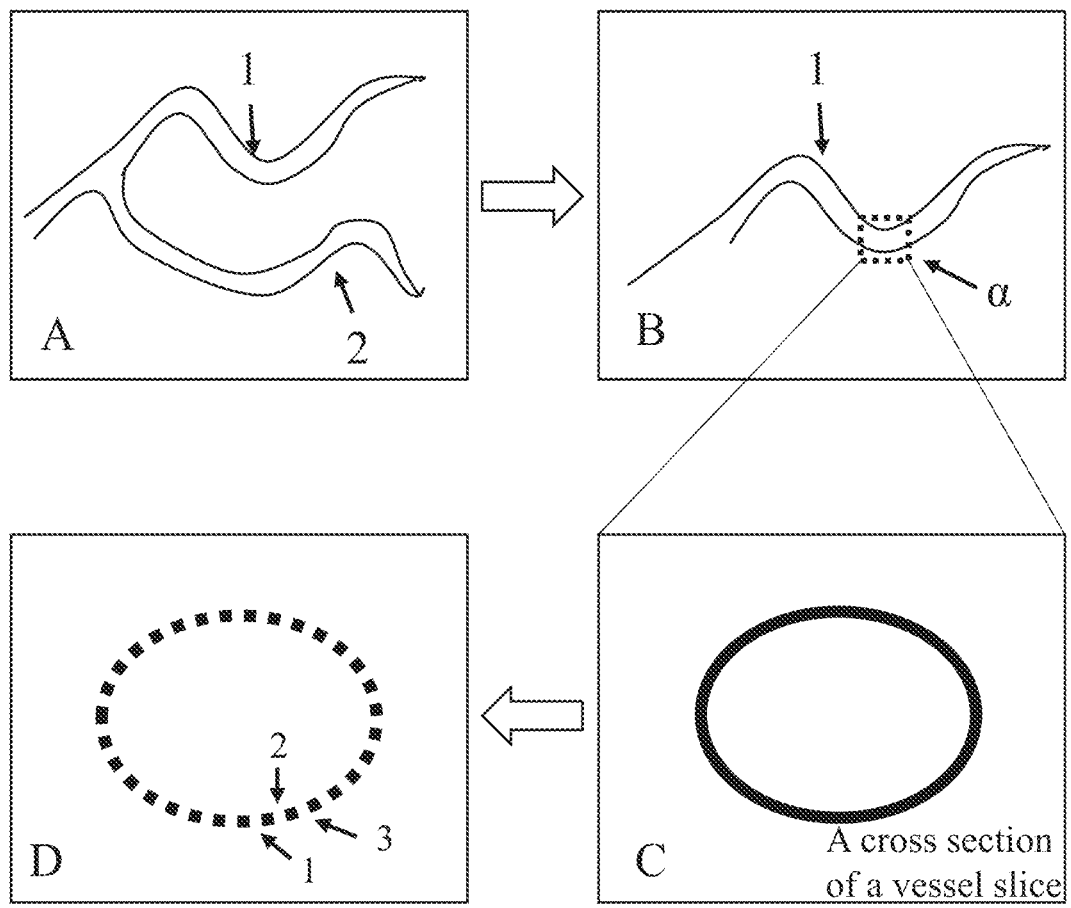
FIG. 12 is a schematic diagram illustrating an example of setting reference points on a vessel model according to some embodiments of the present disclosure.

FIG. 12 is a schematic diagram illustrating an example of setting reference points on a vessel model according to some embodiments of the present disclosure. In image A, the data loading unit 410 reconstructs a three dimensional vessel model according to the vessel image data collected by the data collection device 110. The vessel model includes a vessel 1 and a vessel 2. In some embodiments, the vessel 1 may be a cardiac coronary artery and the vessel 2 may be a cardiac vein. In order to analyze the vessel 1, the vessel 1 and the vessel 2 may need to be separated from each other. In image B, the vessel extraction unit 420 segments the vessel 1 and the vessel 2, and extracts the vessel 1. The segmentation may refer to automatically segmenting the cardiac coronary artery and the cardiac vein. The segmentation may also refer to manually marking and extracting the vessel 1 in the vessel model in image A by the user. In order to study the extracted vessel 1, the vessel 1 may be segmented by the vessel segmentation unit 430. The vessel 1 may be segmented into a plurality of vessel segments according to exemplary techniques for segmenting a vessel described elsewhere in the present disclosure. The vessel segment in the dotted box a may be one of the segmented plurality of vessel segments. If the width of the dotted box a is small enough, the thickness of the vessel segment along the extension direction of the vessel may be ignored. In such a situation, the vessel segment in the dotted box a may be designated as a vessel slice. The cross section of the vessel slice in the dotted box a in the image B may be a closed ring structure. In image C, the contour of the vessel slice may be extracted by the vessel contour determination subunit 720. Exemplary techniques for extracting contours may be found in the description about the vessel contour determination subunit 720. The extracted contour may be a ring-structure curve. The curve may be processed by performing discretization for convenient analysis. In image D, the curve is evenly divided into a plurality of reference points by interpolating at a specific distance. The number of the reference points may be an integer ranging from 50 to 5000, such as 100, 200, etc. In some embodiments, the number of the reference points may be determined by the distance between the reference points. For example, the distance between any two reference points may be determined as a fixed value when setting the reference point. And the number of the reference points may be determined based on the fixed value. After determining the reference points, the reference points may be marked or numbered. For example, the reference point in the bottom of the curve in the image D may be designated as the initial reference point 1. And all the other reference points may be marked or numbered in a counter-clockwise order from the initial reference point 1. In some embodiments, the reference point 1 may be the point closest to the surface of the organ on the vessel slice in terms of a type of vessel (e.g., a vessel on the surface of an organ, etc.). In some embodiments, the reference point 1 may be the point closest to the origin or an axis of the space coordinate system the vessel model locates.

Figure 13:
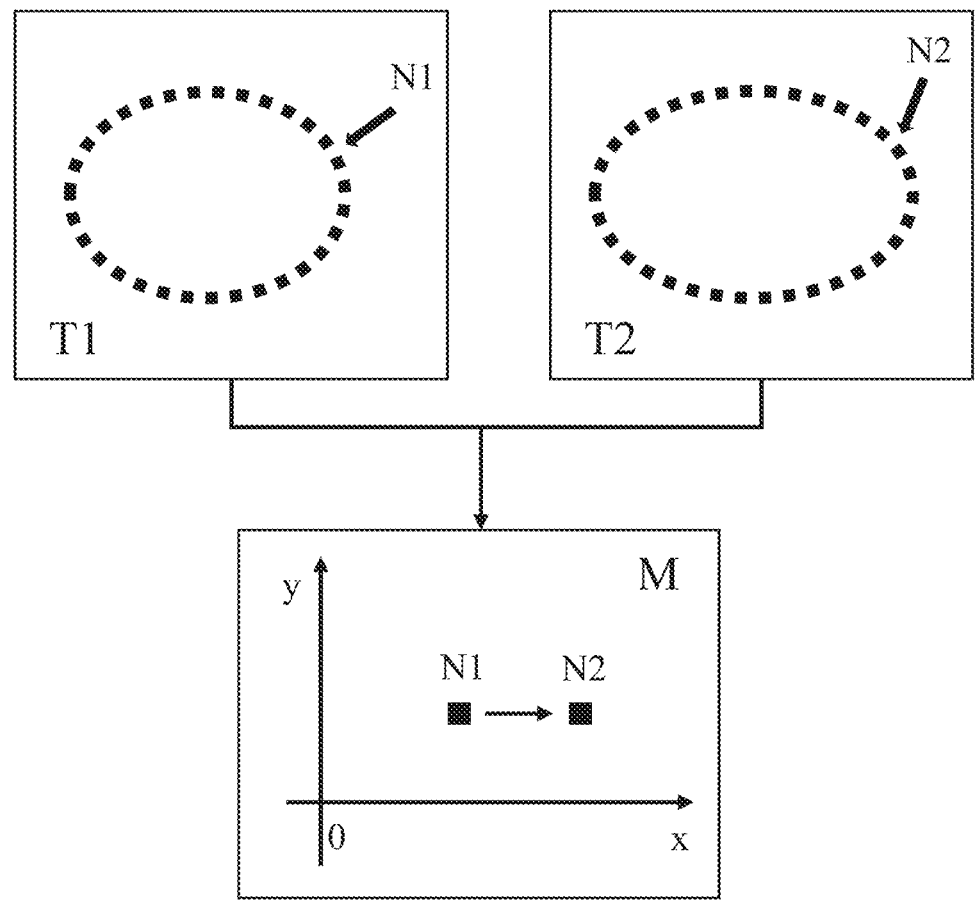
FIG. 13 is a schematic diagram illustrating an exemplary process for determining displacements of reference points based on vessel models of different time phases according to some embodiments of the present disclosure.

FIG. 13 is a schematic diagram illustrating an exemplary process for determining displacements of reference points based on vessel models of different time phases according to some embodiments of the present disclosure. Image T1 and image T2 are two images of a same vessel slice at two different time phases. The contour of the vessel slice and the reference points on the vessel slice are both determined in the two images. A width of the vessel slice increases from T1 to T2 due to some reason. Correspondingly, locations of the reference points on the vessel slice may be changed to some extent. N1 and N2 correspond reference points in T1 and T2. The coordinates of N1 and N2 may be putted into a three dimensional coordinate system M (z axis omitted). Then the displacement from the reference point N1 to the reference point N2 may be determined. The displacement may be indicated by a vector directing from N1 to N2.

According to the schematic diagram, the displacements of all reference points on the vessel slice from time phase T1 to time phase T2 may be determined. In this way, displacements of all reference points on the extracted vessel from time phase T1 to time phase T2 may be determined. And the strain and the stress of the extracted vessel from time phase T1 to time phase T2 may be determined based on the relation between the displacements and the strain as well as the stress. Correspondingly, the strain and the stress of the extracted vessel from time phase T2 to time phase T3 and from time phase T3 to time phase T4 may be determined. After the strain and the stress of the extracted vessel from any adjacent time phases in a cardiac cycle are determined, variation of the strain and the stress on different parts of the vessel within the time period may be determined.

Figure 14:
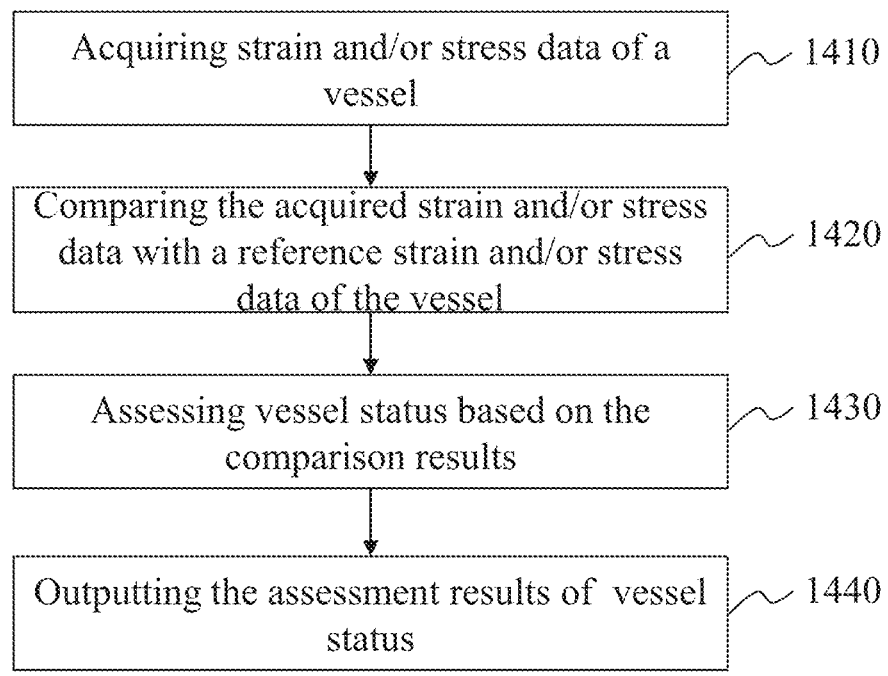
FIG. 14 is a flowchart illustrating an exemplary process for outputting assessment results of vessel status according to some embodiments of the present disclosure.

FIG. 14 is a flowchart illustrating an exemplary process for outputting assessment results of vessel status according to some embodiments of the present disclosure. The process may include acquiring strain and/or stress data of a vessel 1410, comparing the acquired strain and/or stress data with a reference strain and/or stress data of the vessel 1420, assessing vessel status based on the comparison results 1430 and outputting the assessment results of vessel status 1440. In some embodiments, the process may be performed by the analysis module 340.

In 1410, strain and/or stress data may be acquired. The strain and/or stress data may be obtained in 960. In some embodiments, a reference point on a vessel model may have different strains and/or stresses in different time phases. Data indicating the characteristics of the strain and/or stress of the reference point may be the maximal or average strain and/or stress data for the reference point within a time period, or within one or more cardiac cycles. For example, the vessel may have a maximal stress in diagnosis of a vessel disease. The maximal strain and/or stress values for a reference point in different time phases may indicate the characteristics of the strain and/or stress of the reference point. As another example, in some embodiments, a reference point on the vessel may under a certain strain and/or stress for a long time. Then the reference point may have a risk of breaking with the accumulative strain and/or stress. And the average of the accumulative strain and/or stress in different time phases may be designated as the characteristic data of the strain and/or stress of the reference point.

In 1420, the acquired strain and/or stress data may be compared with a reference strain and/or stress data of the vessel. In some embodiments, operation 1420 may be performed by the comparison unit 510. The reference strain and/or stress data of the vessel may be data stored in the storage module 330, data acquired via the network 180, or data provided by the user. In some embodiments, the reference strain and/or stress data of the vessel may be the comparison result of the vessel status described in the comparison unit 510.

In 1430, vessel status may be assessed based on the comparison results. The comparison result of the reference data and the characteristic data of the strain and/or stress of the vessel may correspond to a vessel status such as "normal," "early warning," "dangerous," "extremely dangerous," etc. In some embodiments, the reference data may be some data ranges. The data ranges may correspond to corresponding comparison results, respectively. If the characteristic data of the strain and/or stress of the vessel falls within a data range, the vessel status may be the corresponding comparison result. Operation 1430 may be performed by the generation unit 520 to generate a statistical graph, a statistical chart, a text with fixed format, an audio, or the like, or a combination thereof. Exemplary techniques for generating the files may be found in the description about the generation unit 520.

In 1440, the assessment results of vessel status may be output. In some embodiments, operation 1440 may be performed by the transmission unit 530. Exemplary techniques for outputting the assessment results of the vessel status may be found in the description about the transmission unit 530.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method, implemented on at least a device including a processor and a storage, comprising:
   acquiring first vessel data of a first time phase corresponding to a vessel;
   acquiring second vessel data of a second time phase corresponding to the vessel;
   generating, based on the first vessel data, a first vessel model relating to the first time phase;
   generating, based on the second vessel data, a second vessel model relating to the second time phase;
   determining a reference point in the first vessel model and a first coordinate of the reference point in the first vessel model in a space coordinate system the vessel model locates;
   determining the reference point in the second vessel model and a second coordinate of the reference point in the second vessel model in the space coordinate system;
   determining a displacement of the reference point from the first vessel model to the second vessel model, the displacement being a space vector directing from the first coordinate to the second coordinate; and
   determining a strain change or a stress change at the reference point based on the displacement,
   wherein the determining the reference point in the second vessel model comprises:
   dividing the first vessel model into a first plurality of vessel slices, and the second vessel model into a second plurality of vessel slices;
   extracting a contour of a vessel slice of the first plurality of vessel slices and a contour of a corresponding vessel slice of the second plurality of vessel slices;
   determining a plurality of candidate reference points at a same distance interval on the contour of the vessel slice and on the contour of the corresponding vessel slice;
   determining an initial point in the plurality of candidate reference points, the initial point being closest to an origin or an axis of the space coordinate system the vessel model locates;
   numbering the plurality of candidate reference points in a clockwise or counterclockwise sequence from the initial point; and
   determining a candidate reference point on the contour of the corresponding vessel slice having a same number of the reference point on the contour of the vessel slice of the first vessel model as the reference point in the second vessel model.

2. The method of claim 1, wherein the first time phase and the second time phase are within an entire cardiac cycle, and the second time phase immediately following the first time phase.

3. The method of claim 2, further comprising:
   determining continuous displacements of the reference point between two adjacent time phases of the cardiac cycle; and
   determining a continuous strain change or a continuous stress change at the reference point in the entire cardiac cycle based on the continuous displacements.

4. The method of claim 3, further comprising:
   comparing a maximum principal strain or a maximum principal stress at the reference point with a reference data;
   determining a vessel status based on the comparison; and
   providing the vessel status to a user.

5. The method of claim 4, further comprising presenting the vessel status in at least one form of an image, a chart, text with a fixed format, or audio.

6. The method of claim 4, further comprising retrieving the reference data from a storage device.

7. The method of claim 4, wherein the providing the determined vessel status to a user includes sending the vessel status to a user terminal.

8. The method of claim 4, wherein the comparing the maximum principal strain or the maximum principal stress at the reference point with a reference value includes:
   determining a characteristic of the maximum principal strain or the maximum principal stress at the reference point; and
   comparing the characteristic with the reference data.

9. The method of claim 8, wherein the characteristic of the maximum principal strain or the maximum principal stress at the reference point includes a maximal value of the maximum principal strains or stresses at the reference point at different time phases.

10. The method of claim 8, wherein the characteristic of the maximum principal strain or the maximum principal stress at the reference point includes an average value of the maximum principal strains or stresses at the reference point in different time phases.

11. The method of claim 3, further comprising:
    generating an animation that presents the continuous strain change or stress change in the entire cardiac cycle; and
    transmitting the animation to a user terminal for displaying on the user terminal.

12. The method of claim 1, wherein the dividing the first vessel model into a plurality of vessel slices includes:
    determining a center line of the first vessel model;
    dividing the center line into a plurality of center line segments; and
    determining a vessel segment corresponding to a center line segment of the plurality of center line segments as a vessel slice.

13. The method of claim 1, further comprising:
    determining a region of interest in the first vessel model; and
    determining a region of interest in the second vessel model,
    wherein the reference point is in the region of interest.

14. The method of claim 13, the dividing the first vessel model into a first plurality of vessel slices, and the second vessel model into a second plurality of vessel slices further comprising:
    dividing the region of interest in first vessel model into the first plurality of vessel slices; and
    dividing the region of interest in the second vessel model into the plurality of vessel slices.

15. The method of claim 13, wherein the first vessel model includes a cardiovascular model, including a coronary artery and a vein; and the determining a region of interest in the first vessel model includes automatically determining the coronary artery in the cardiovascular model.

16. The method of claim 13, wherein the determining a region of interest in the first vessel model includes:
    determining two points along a center line of a first vessel; and
    extracting a vessel segment between the two points.

17. A system comprising:
at least one processor; and
a storage medium configured to store instructions, wherein when executing the instructions, the at least one processor is configured to cause the system to:
acquire first vessel data of a first time phase corresponding to a vessel;
acquire second vessel data of a second time phase corresponding to the vessel;
generate, based on the first vessel data, a first vessel model relating to the first time phase;
generate, based on the second vessel data, a second vessel model relating to the second time phase;
determine a reference point in the first vessel model and a first coordinate of the reference point in the first vessel model in a space coordinate system the vessel model locates;
determine the reference point in the second vessel model and a second coordinate of the reference point in the second vessel model in the space coordinate system;
determine a displacement of the reference point from the first vessel model to the second vessel model, the displacement being a space vector directing from the first coordinate to the second coordinate; and
determine a strain change or a stress change at the reference point based on the displacement,
wherein to determine the reference point in the second vessel model, the at least one processor is configured to cause the system further to:
divide the first vessel model into a first plurality of vessel slices, and the second vessel model into a second plurality of vessel slices;
extract a contour of a vessel slice of the first plurality of vessel slices and a contour of a corresponding vessel slice of the second plurality of vessel slices;
determine a plurality of candidate reference points at a same distance interval on the contour of the vessel slice and on the contour of the corresponding vessel slice;
determine an initial point in the plurality of candidate reference points, the initial point being closest to an origin or an axis of the space coordinate system the vessel model locates;
number the plurality of candidate reference points in a clockwise or counterclockwise sequence from the initial point; and
determine a candidate reference point on the contour of the corresponding vessel slice having a same number of the reference point on the contour of the vessel slice of the first vessel model as the reference point in the second vessel model.

18. The system of claim 17, wherein the first time phase and the second time phase are within an entire cardiac cycle, and the second time phase immediately following the first time phase.

19. The system of claim 18, wherein the at least one processor is configured to cause the system further to:

determine continuous displacements of the reference point between two adjacent time phases of the cardiac cycle; and
determine a continuous strain change or a continuous stress change at the reference point in the entire cardiac cycle based on the continuous displacements.

20. A non-transitory computer readable medium embodying a computer program product, the computer program product comprising instructions, when executed by at least processer causing the at least one processer to effectuate a method comprising:
acquiring first vessel data of a first time phase corresponding to a vessel;
acquiring second vessel data of a second time phase corresponding to the vessel;
generating, based on the first vessel data, a first vessel model relating to the first time phase;
generating, based on the second vessel data, a second vessel model relating to the second time phase;
determining a reference point in the first vessel model and a first coordinate of the reference point in the first vessel model in a space coordinate system the vessel model locates;
determining the reference point in the second vessel model and a second coordinate of the reference point in the second vessel model in the space coordinate system;
determining a displacement of the reference point from the first vessel model to the second vessel model, the displacement being a space vector directing from the first coordinate to the second coordinate; and
determining a strain change or a stress change at the reference point based on the displacement,
wherein the determining the reference point in the second vessel model comprises:
dividing the first vessel model into a first plurality of vessel slices, and the second vessel model into a second plurality of vessel slices;
extracting a contour of a vessel slice of the first plurality of vessel slices and a contour of a corresponding vessel slice of the second plurality of vessel slices;
determining a plurality of candidate reference points at a same distance interval on the contour of the vessel slice and on the contour of the corresponding vessel slice;
determining an initial point in the plurality of candidate reference points, the initial point being closest to an origin or an axis of the space coordinate system the vessel model locates;
numbering the plurality of candidate reference points in a clockwise or counterclockwise sequence from the initial point; and
determining a candidate reference point on the contour of the corresponding vessel slice having a same number of the reference point on the contour of the vessel slice of the first vessel model as the reference point in the second vessel model.

* * * * *